(12) United States Patent
Ben Noon et al.

(10) Patent No.: US 11,793,919 B2
(45) Date of Patent: Oct. 24, 2023

(54) EXTRACORPOREAL OXYGENATION SYSTEM FOR LOW FLOW RATES AND METHODS OF USE

(71) Applicant: Inspira-Technologies OXY B.H.N. LTD., Ra'anana (IL)

(72) Inventors: Dagi Ben Noon, Burgata (IL); Abraham Shabtay, Tel-Aviv (IL)

(73) Assignee: Inspira-Technologies OXY B.H.N. LTD., Ra'anana (IL)

( * ) Notice: Subject to any disclaimer, the term of this patent is extended or adjusted under 35 U.S.C. 154(b) by 0 days.

(21) Appl. No.: 17/905,413

(22) PCT Filed: Dec. 1, 2021

(86) PCT No.: PCT/IL2021/051431
§ 371 (c)(1),
(2) Date: Sep. 1, 2022

(87) PCT Pub. No.: WO2022/118314
PCT Pub. Date: Jun. 9, 2022

(65) Prior Publication Data
US 2023/0118378 A1    Apr. 20, 2023

Related U.S. Application Data

(60) Provisional application No. 63/167,226, filed on Mar. 29, 2021, provisional application No. 63/123,809, filed on Dec. 10, 2020, provisional application No. 63/119,997, filed on Dec. 1, 2020.

(51) Int. Cl.
| | |
|---|---|
| *A61M 1/36* | (2006.01) |
| *A61M 1/30* | (2006.01) |
| *A61M 1/32* | (2006.01) |
| *A61M 5/158* | (2006.01) |
| *A61M 5/36* | (2006.01) |
| *A61M 5/00* | (2006.01) |
| *A61M 1/14* | (2006.01) |
| *A61M 5/14* | (2006.01) |

(52) U.S. Cl.
CPC ............ *A61M 1/3644* (2014.02); *A61M 1/15* (2022.05); *A61M 1/30* (2013.01); *A61M 1/32* (2013.01); *A61M 1/3622* (2022.05); *A61M 1/3629* (2014.02); *A61M 1/3643* (2013.01); *A61M 5/002* (2013.01); *A61M 5/1582* (2013.01); *A61M 5/36* (2013.01); *A61M 2005/1402* (2013.01); *A61M 2205/3331* (2013.01)

(58) Field of Classification Search
CPC ............ A61M 1/15; A61M 1/30; A61M 1/32; A61M 1/3622; A61M 1/3629; A61M 1/3643; A61M 1/3644; A61M 5/002; A61M 5/1582; A61M 5/36; A61M 2005/1402; A61M 2205/3331
See application file for complete search history.

(56) References Cited

U.S. PATENT DOCUMENTS

| | | |
|---|---|---|
| 2010/0114005 A1 | 5/2010 | Rovatti |
| 2014/0099235 A1 | 4/2014 | Ellingboe |
| 2020/0009331 A1 | 1/2020 | Kamen |

OTHER PUBLICATIONS

International Search Report dated Apr. 12, 2022 for Application No. PCT/IL2021/051431.

*Primary Examiner* — John Kim
(74) *Attorney, Agent, or Firm* — Maxwell L. Minch; Maxwell L Minch Esq. PA

(57) ABSTRACT

This invention is directed to system and methods for the oxygenation of the blood of a patient, comprising an extracorporeal blood circulation path adapted to be coupled to the patient's vascular system, and comprising apparatus for oxygenating blood flowing therein and withdrawing CO2 therefrom, wherein the flow rate of blood flowing in said extracorporeal blood circulation path does not exceed ⅖ of the patient's blood flow. The extracorporeal blood circulation path preferably comprise a cartridge including an oxygenator and at least one cannula.

9 Claims, 10 Drawing Sheets

EXTRACORPOREAL OXYGENATION SYSTEM FOR LOW FLOW RATES AND METHODS OF USE

FIELD OF THE INVENTION

The present disclosure concerns system and methods for treating respiratory failure by extracorporeal oxygenation system. More specifically, the present disclosure is directed to a novel extracorporeal oxygenation system for awake and spontaneously breathing patients in low flow rates, and to methods of use.

BACKGROUND OF THE INVENTION

Patients suffering from respiratory failure are often treated by highly invasive mechanical ventilation systems, which are used to replace spontaneous breathing by employing pressure (positive or negative) to force air into the failing or nonfunctional lungs of the patient. Although being considered a life-saving intervention necessary for treating highly dysfunctional lungs or unconscious patients suffering from respiratory failure, the use of such systems is often viewed as a high-risk procedure with increased probability of various complications, such as airway injury, pneumothorax, various airways infections, acute respiratory distress syndrome (ARDS), etc. Due to the highly invasive intubation required for mechanical ventilation, such systems are typically used on unconscious patients or patients under complete sedation.

A complementary procedure to mechanical ventilation is the use of extracorporeal oxygenation systems, such as extracorporeal membrane oxygenation (ECMO) systems, which are lung or lung-heart bypass systems for extracorporeally circulating the blood of the patient to remove carbon dioxide ($CO_2$) and increase oxygenation of the blood. As such systems typically require fast circulation of the entire volume of the patient's blood, these also are considered high-risk procedures, typically requiring full sedation of patients during treatment.

Extracorporeal oxygenation machines are used to oxygenate blood outside a patient's body. During a process of extracorporeal oxygenation, a cannula is inserted into a patient's vascular system, for example, at the superior vena cava or the internal jugular vein. A cannula is a tube that may be inserted into the body, such as for delivering and removing fluid. Cannulas may be used to add to and remove blood from a patient's vascular system. Prior to the insertion of a cannula into the vascular system, it is necessary to prime the cannula by evacuating all air therefrom. Priming the cannula and priming all sterile tubing in the fluid flow path connected to the cannula is necessary because the insertion of air bubbles into the vascular system causes air embolisms, which are dangerous and may even be fatal. Typically, a technician primes the cannula manually by introducing saline into the cannula until it is filled with saline. For example, the technician may connect a saline bag to the cannula with two tubes and fill the cannula and tubes through gravitation. Cannulas having two lumens are also available in the market. Such cannula is described in detail in PCT/IL2021/051335 of the same inventors and is incorporated herein by reference. In such a scenario, deoxygenated blood leaves the body via a drainage lumen into the extracorporeal system, is oxygenated with an oxygenator, and is returned to the body via an infusion lumen. Extracorporeal oxygenation systems known to date currently include two separate components: a cannula and an oxygenation kit with tubing. Each of these components is separately primed prior to commencement of the oxygenation. After the cannulation of the cannula into the body, the cannula is connected to the tubes from the oxygenation kit. The technician washes the connection point to prevent air from getting into the connection area. In some optional embodiments of this invention, an automatic priming system for the cannula and tubes connected therethrough is provided.

Preparing the system for extracorporeal oxygenation of blood for operation is a complicated process that requires well-trained technicians as any mistake can result in a life-threatening situation. In addition, connecting the various tubes to the pumps and assembling the system until it is ready to use is time-consuming when every second that the patient is suffering from respiratory failure may be critical. Thus, a simplified, fast and safe process for assembling the system, that can minimize the chances for human errors and increase the safety of the patient, and reduce the time required by the medical team to prepare the system for use is required.

Non-invasive ventilation (NIV) refers to the delivery of positive pressure ventilation through a non-invasive interface (e.g., BIPAP, CPAP, nasal mask, face mask, oxygen helmet, nasal prongs), rather than an invasive ventilation approach (endotracheal tube, tracheostomy). The decision to move from non-invasive to invasive ventilation involves several factors, including the patient's ability to maintain airway patency, his/her ability to ventilate and oxygenate as well as the patients' expected clinical course. Adverse pulmonary effects of invasive ventilation include pulmonary barotrauma, ventilator-associated lung injury, ventilator-associated pneumonia intrinsic positive end expiratory pressure (auto-PEEP), heterogeneous ventilation, altered ventilator/perfusion mismatch (increased dead space, decreased shunt), diaphragmatic muscle atrophy, respiratory muscle weakness, and diminished mucociliary motility.

Invasive ventilation may reduce cardiac output and impair hemodynamic stability. In addition, it is associated with gastrointestinal stress ulceration, decreased splanchnic perfusion, gastrointestinal hypomotility, fluid retention, acute renal failure, increased intracranial pressure, weakness, inflammation, and disordered sleep.

The present invention is intended to be used to increase blood oxygenation level and remove $CO_2$ in order to prevent or delay invasive ventilation and minimize the associated adverse pulmonary effects.

SUMMARY OF THE INVENTION

According to one main aspect of the invention, a system for extracorporeal oxygenation of blood in low flow rates of up to 30 ml/Kg per minute is disclosed. The novel extracorporeal oxygenation system provided herein is preferably used for acute respiratory failure patients treated with non-invasive ventilation as they still exhibit spontaneous breathing and uses a blood circulation rate of no more than 30 ml/kg per minute. This circulation rate is much lower than the circulation rate used in ECMO that ranges between 60-80 ml/kg/min for V-V (veno-venous) ECMO and 50-60 ml/kg/min for V-A (veno-arterial) ECMO ("*Extracorporeal Life Support: The ELSO Red Book*", 5th Edition, p. 75). In general, target flow rates in ECMO are: 100-150 ml/kg/min (neonates), 80-100 ml/kg/min (pediatrics), and 60 ml/kg/min (adults). In V-V support, blood flow rates are typically higher than V-A, 120 ml/kg/min for neonates ranging downward to 60-80 ml/kg/min for adults. The system and methods of the present invention may further be used for increasing blood oxygenation level and $CO_2$ removal in mechanically ventilated (MV) patients, not considered candidates for ECMO, based on the level of severity as defined by the patient PaO2/FiO2 ratio.

The inventors of the present invention have come to the surprising finding that reduced volume circulation of the patient's blood and oxygenation of only a portion of the blood, and not its entire volume or most of the volume, can improve respiration of conscious patients that are still capable of spontaneous breathing, reduce discomfort and minimize the risk of complications. The novel system is designed to support a functioning (yet sick) lung(s), and to work in tandem with a patient who is awake and breathing on his/her own accord, albeit at a reduced capacity. The novel system provided herein is aimed to supplement the oxygen in the blood, which is insufficient due to underperforming lungs. This is a major point of difference in acute respiratory care, as in contrast to ECMO that requires the lung being "shut down" and therefore requires the entire replacement of lung functionality, the extracorporeal blood oxygenation system and methods of the present invention allows the lung to be left alone and treated by the medical team, instead of overburdening it with Mechanical Ventilation.

The novel system provided herein for extracorporeal blood oxygenation is aimed to operate in low flow rates such as, but not limited to 30 ml/kg per minute as compared to an average of about 60-80 ml/kg/min blood flow rate in standard ECMO use. In some optional embodiments, the novel system is configured to use higher pressure drop to cause higher flow speed and prevent clotting. The system provided herein may further control the sweep gas flow. As the system is configured to work on low blood flow rates and 100% FiO2, the carbon dioxide transfer rate can be controlled and maximized by using higher gas to blood flow ratio, without lowering the blood oxygenation as in ECMO systems. ECMO systems can't use a high ratio since it will lower the blood oxygenation capacity, but since the novel system is configured to oxygenate only low flow rates, such as for example (but not limited to) 1 L/min and to operate over the blood saturation point it can lower the oxygen transfer rate and raise the CO2 removal level.

Blood oxygenation level (also referred to as oxygen saturation level) denotes the oxygen-saturated hemoglobin out of the total hemoglobin in the blood. A normal blood oxygenation level in humans is between about 95-100%. Typically, saturation levels below 90% are considered a state of hypoxemia, with patients often being required to be connected to mechanical ventilation systems to prevent compromising organ function or causing organ failure.

Extracorporeal blood-oxygenation systems are systems typically linked to veins or arteries to circulate blood extracorporeally, by draining blood through a blood vessel (a vein or an artery) using a pump, passing it through an external oxygenator to reduce carbon dioxide ($CO_2$) levels and enrich the blood with oxygen, following which blood is infused back into the patient's circulatory system. The link between the extracorporeal blood oxygenation system and the patient is carried out via the insertion of one or more cannulas into one or more blood vessels of the patient. A cannula is a thin tube inserted into the blood vessel that permits extraction or infusion of blood therethrough from/into the blood vessel. The cannulas used in methods according to the invention are typically selected to be of a minimal possible size that will permit the required blood flow rate for obtaining the desired oxygenation level. In the methods of this disclosure, the cannula's size may be selected by considering the required blood flow according to the patient's weight that is indicative of the cardiac output of each patient.

As noted, extraction and infusion of blood can be through veins or arteries of the patient, for example, the internal jugular vein, the femoral vein, the subclavian vein, the jugular artery, the femoral artery, and the subclavian artery of the patient. In the methods of this disclosure utilizing two separate cannulas (i.e., dual-site cannulation), the first blood vessel may, in some embodiments, be the femoral vein, and the second blood vessel may be the internal jugular vein of the patient. In methods of this disclosure utilizing a dual-lumen cannula (i.e., single-site cannulation), the blood vessel may be the internal jugular vein, femoral vein, subclavian vein, the jugular artery, the femoral artery, and the subclavian artery of the patient.

The methods of this disclosure are designed for use in conscious, i.e., non-sedated (or non-anesthetized) patients who exhibit spontaneous breathing with partial lung functioning. Hence, methods of this disclosure provide oxygenation solutions to a population of patients that are still presenting spontaneous breathing even if not entirely effective. The inventors have realized that in such patients, oxygenation of only a portion of blood at low flow rates, in combination with spontaneous breathing, is sufficient to significantly raise blood oxygenation and support treatment of at least partial respiratory failure (and at times, of full respiratory failure). The combination of efficient external oxygenation of a portion of the blood, together with the contribution of the residual gas exchange of the failing lung, permits sufficient depletion of $CO_2$ and oxygen enrichment to elevate the oxygen saturation levels of the patient to normal values during treatment.

Thus, the circulation rate of blood utilized in the methods of this disclosure is at most about 30 ml/kg per minute (i.e., no more than ⅖ of the average blood flow of a patient).

Hence, in some embodiments, the methods further comprise determining at least one of (i) blood circulation rate and (ii) size of cannula(s), said determination being based on said patient's weight or BSA (Body Surface Area) according to common practice. After the flow rate is determined, the cannula size is chosen according to the cannulation area and the circulation flow that reflects up to 30 ml/kg per minute. Such determinations can be carried out in a controller of the extracorporeal blood oxygenation system, which receives input in the form of the patient's physical parameters and provides determination of the proper cannula size and blood flow rate to be used. Alternatively, it may be conducted manually.

The methods can further comprise monitoring and/or receiving input and/or reading from various sensors associated with the extracorporeal blood oxygenation system providing readings and data concerning various patient parameters, e.g., oxygen saturation levels, pH, blood pressure, pressures in the system, blood flow rate, active clotting time, blood temperature, cardiac output, partial pressure of oxygen and $CO_2$, hemoglobin concentration, and others. These monitored parameters are then utilized by the controller of the system to modify or adjust the circulation rate of blood, or other definitive aspects of the system, to obtain the desired target oxygenation level.

As noted above, the methods of this disclosure are intended for treating conscious, spontaneously breathing patients suffering from partial lung failure. However, methods of this disclosure can also be used to treat patients simultaneously treated by mechanical ventilation. Thus, in another aspect, this disclosure provides a method of increasing blood oxygenation level and $CO_2$ removal in a patient suffering from at least partial respiratory failure, the method comprising introducing a first cannula into a first blood vessel for draining blood therefrom, and a second cannula into a second blood vessel for infusing oxygenated blood thereto, the first and second cannulas being linked to an extracorporeal blood-oxygenation system through a first flow line and a second flow line, respectively, and circulating said patient's blood at a circulation rate of no more than about 30 ml/kg per minute through said extracorporeal blood-oxygenation system to oxygenate said blood and obtain $CO_2$ removal from the blood and an increase in blood oxygenation level of the patient, the patient being simultaneously treated with mechanical ventilation.

The present invention in one another implementation is aimed to provide a system for extracorporeal oxygenation of blood that includes a reusable base and a single-use cartridge. The reusable base may include a controller and a plurality of pump drive units. The single-use cartridge includes one or more pump heads. Each pump head is controllable by a respective pump drive unit when the cartridge is installed in the base. The single-use cartridge further includes an oxygenator and optionally at least one cannula. When the cartridge is installed in the base, the controller is configured to pump blood from the patient vascular system through a sterile flow path defined by the at least one cannula, sterile tubing, a plurality of pump heads, and an oxygenator, and to oxygenate the pumped blood.

The disposable cartridge is preferably a single unit plug-and-play kit having minimal parts that can contribute to clotting development. Preferably, all parts of the cartridge are anti-coagulant material coated. The system provided herein has a higher pressure drop causing higher flow speed and preventing clotting. Additionally, the system is a low blood flow system; thus, it doesn't require high anticoagulation levels (much closer to dialysis systems).

The novel system may comprise various sensors and indicators (non-invasive) to indicate blood flow, blood pressure (pre and post membrane), blood temperature, CO2 levels, SVo2 (venous saturation) levels, cardiac output, ACT, and other clotting values.

Manual priming of cannulas requires a technician to have sufficient skill to perform the priming operation properly. If the priming operation is not performed properly, the patient may be endangered. In addition, manual priming requires a considerable amount of time.

Accordingly, it is an object of the present disclosure to provide an automatic priming system for a cannula. The automatic priming system primes a cannula automatically upon connection of a cartridge containing the cannula to the system. Advantageously, the automatic priming system obviates the need for manual priming, saving time and reducing the potential risks resulting from human error.

It is a further object of the present disclosure to provide an automatic priming system as part of an extracorporeal oxygenation system, such that the same machine may be used to automatically prime the cannula and perform extracorporeal oxygenation. Furthermore, it is an object of the present disclosure to provide a cartridge that integrates the cannula with the oxygenation system so that there is no need to connect the cannula to the kit following cannulation.

According to some aspects, a system for automatic priming of at least one cannula is disclosed. The system includes a priming cap including an inlet and an outlet that are sealed from each other, a saline repository, a priming pump comprising a drive unit and a replaceable priming pump head, and a fluid path comprising sterile tubing between a first lumen and second lumen of the at least one cannula, the fluid path not including the priming cap. The priming cap is removably fittable over the first and second lumens, such that, when the priming cap is fitted over the first and second lumens, the inlet is in fluid communication with the first lumen of the at least one cannula, and the outlet is in fluid communication with the second lumen of the at least one cannula, such that the at least one cannula, priming cap, saline repository, priming pump head, and fluid path form a closed loop for fluid flow. When the priming cap is not fitted over the at least one cannula, the at least one cannula is insertable into a patient vascular system. A controller is configured to operate the priming pump when the priming cap is fitted over the at least one cannula, and thereby evacuate air from the closed loop. Advantageously, the system is able to prime the at least one cannula while the cannula remains within the closed loop and without exposing the cannula to ambient atmosphere.

In another implementation of the invention, the at least one cannula, priming cap, the saline repository, the priming pump head, and the fluid path are contained within a cartridge. The cartridge is attachable to and removable from a base containing the controller. Advantageously, the cartridge may be disposed of after each use, while the controller may be included as part of a reusable base.

Optionally, the controller is configured to commence a priming operation automatically upon attachment of the cartridge to the base. Advantageously, the automatic commencement avoids the possibility of error resulting from manual priming.

Optionally, the system further includes a sterile patient penetration kit, including an introducer, one or more dilators, and a guidewire. Optionally, the controller is configured to operate the priming pump while the sterile patient penetration kit remains hermetically sealed. Thus, the priming operation may be completed without a potential for contaminating the items in the patient penetration kit.

In another implementation according to the invention, the fluid path includes an oxygenation system. Thus, the automatic priming system may be used to prime an oxygenation system, for extracorporeal oxygenation.

Optionally, the first and second lumens comprise a drainage lumen and an infusion lumen. When the at least one cannula is inserted into a patient vascular system, the oxygenation system is configured to oxygenate blood withdrawn via the drainage lumen and return oxygenated blood via the infusion lumen. Thus, deoxygenated blood and oxygenated blood are transported between the patient vascular system and the system via separate lumens.

In another implementation according to the first aspect, the at least one cannula comprises a dual lumen cannula. Optionally, the dual lumen cannula includes a first lumen and a second lumen arranged side by side, and an extent of the first lumen is greater than a corresponding extent of the second lumen. Advantageously, this arrangement permits the priming cap to be arranged over the dual lumen cannula with different regions fluidically connected to the different lumens. Optionally, the dual lumen cannula further includes a sheath for guiding the dual lumen cannula along a guidewire. The sheath is used to place the dual lumen cannula at a desired location within the patient vascular system.

In another implementation of the invention, the closed loop includes, in order, the first lumen, the fluid path, the second lumen, an inlet of the priming cap, the saline repository, the priming pump head, an outlet of the priming cap, and again the first lumen.

According to another aspect, a method of automatic priming of at least one cannula is disclosed. The method includes attaching a cartridge to a base of an automatic priming system. The automatic priming system includes a priming cap including an inlet and an outlet that are sealed from each other, a saline repository, a priming pump comprising a drive unit and a replaceable priming pump head, and a fluid path comprising sterile tubing between a first lumen and second lumen of the at least one cannula, the fluid path not including the priming cap. The priming cap is removably fittable over the at least one cannula, such that, when the priming cap is fitted over the at least one cannula, the inlet is in fluid communication with the first lumen of the at least one cannula, and the outlet is in fluid communication with the second lumen of the at least one cannula, such that the at least one cannula, priming cap, saline repository, priming pump head, and fluid path form a closed loop for fluid flow. When the priming cap is not fitted over the at least one cannula, the at least one cannula is insertable into a patient vascular system. The cartridge comprises the at least one cannula, priming cap, saline repository, the priming pump head, and the fluid path. The method further comprises operating the priming pump when the priming cap is fitted over the at least one cannula to thereby evacuate air from the entire closed loop.

In another implementation, the method further comprises commencing a priming operation automatically upon attachment of the cartridge to the base. Optionally, the automatic priming system further comprises a sterile patient penetration kit including an introducer, one or more dilators, and a guidewire, and the method further comprises performing the operating step while the sterile patient penetration kit remains hermetically sealed.

In another implementation of the invention, the at least one cannula is a dual lumen cannula. The method further includes: penetrating a patient vascular system with an introducer, one or more dilators, and a guidewire; extending the guidewire within the patient vascular system to a target location; expanding a vessel of the patient vascular system with the one or more dilators such that the vessel is expanded to receive therein the dual lumen cannula; removing the priming cap from the dual lumen cannula; guiding a sheath of the dual lumen cannula along the guidewire to the target location; removing the introducer, one or more dilators, and the guidewire; and closing the sheath of the dual lumen cannula.

Optionally, the fluid path includes an oxygenation system, and the first and second lumens include a drainage lumen and an infusion lumen. The method further includes removing deoxygenated blood from the patient vascular system via the drainage lumen, oxygenating the deoxygenated blood with the oxygenation system, and returning oxygenated blood to the patient vascular system via the infusion lumen.

Optionally, the method further includes performing the removing, oxygenating, and returning steps while circulating the blood through the fluid path at a rate no greater than approximately 30 ml/kg per minute. This rate is suitable for supplemental oxygenation of a patient who is capable of independent breathing.

BRIEF DESCRIPTION OF THE DRAWINGS

Examples illustrative of embodiments of the disclosure are described below with reference to figures attached hereto. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings.

In the drawings.

DETAILED DESCRIPTION OF EMBODIMENTS AND EXAMPLES

Figure 1A:
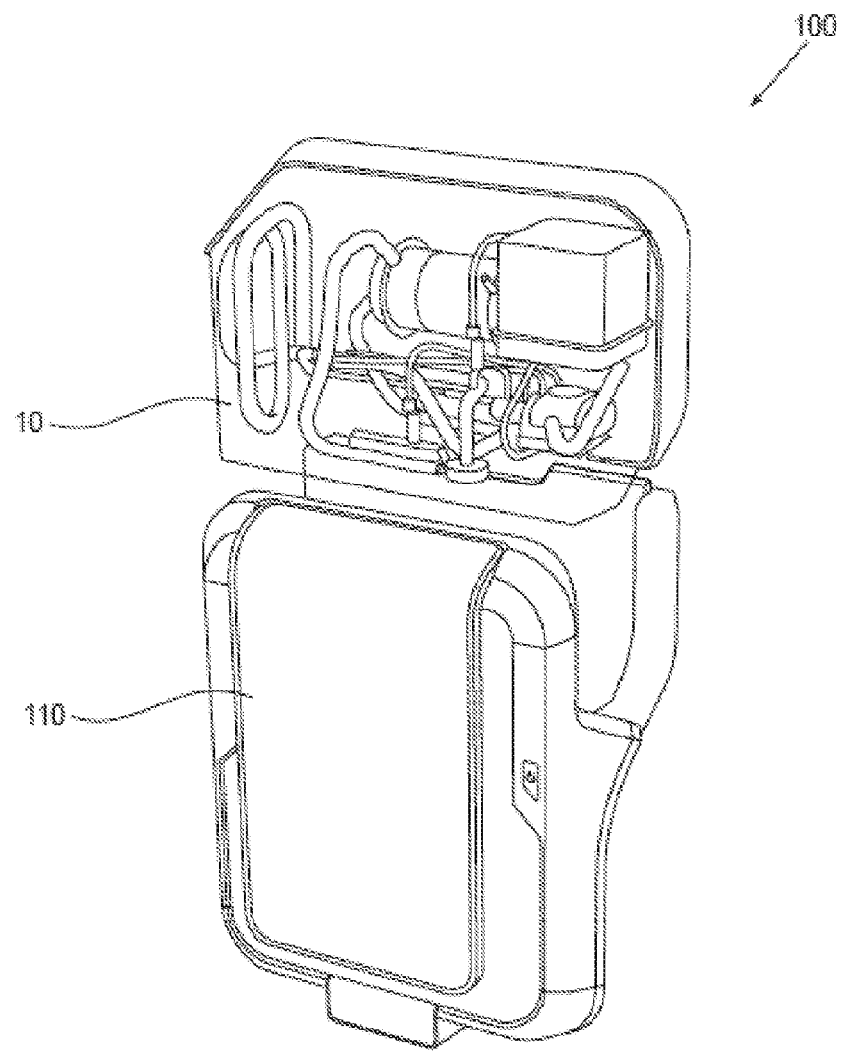
FIG. 1A is a schematic isometric front view illustration of an extracorporeal oxygenation system, with base and cartridge before connection form according to embodiments of the present disclosure.

In the following description, various aspects of the novel extracorporeal oxygenation system and methods of use will be described. For the purpose of explanation, specific configurations and details are set forth in order to provide a thorough understanding of the invention.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below. The descriptions, examples and materials presented in the description, as well as in the claims, should not be construed as limiting, but rather as illustrative.

In one aspect, the present invention is directed to a system for the oxygenation of the blood of a patient, comprising an extracorporeal blood circulation path adapted to be coupled to the patient's vascular system, and comprising apparatus for oxygenating blood flowing therein and withdrawing $CO_2$ therefrom, wherein the flow rate of blood flowing in said extracorporeal blood circulation path does not exceed $\frac{2}{5}$ of the patient's blood flow. In accordance with embodiments of the invention, the flow rate is not greater than 30 ml/kg per minute. The system may comprise within the extracorporeal blood circulation path a cartridge including an oxygenator and at least one cannula. In such embodiment, the cartridge may comprise disposable components that are being in contact with the blood of the patient during extracorporeal blood circulation. The cartridge is configured and operable to be reversibly connected to a reusable base having at least a controller, and one or more pump drive unit and motor, said drive unit and motor is respective to a pump head positioned in the cartridge, and a power source. The base may further comprise at least one fixed sensor and/or a user interface. In some embodiments, the cartridge comprising one or more pump heads, each pump head being controllable by a respective pump drive unit and a motor within the base.

Optionally, the extracorporeal blood circulation path is provided with an auto priming system adapted to ensure a safe, emboli-free connection to the patient's vascular system. In such scenario, the cartridge may further comprise a saline repository connected to the auto priming system.

The present invention is further directed to a cartridge for extracorporeal blood oxygenation, comprising a one or more pump heads, each pump head being controllable by a respective pump drive unit, an oxygenator, and at least one cannula. When a single cannula is provided, it is a dual cannula. Preferably, all surfaces coming into contact with blood are anti-coagulant coated. The disposable cartridge is configured to be plugged onto a complementary base before usage, said complementary base control and operate the cartridge components.

In a further aspect of the invention a method for supporting a patient having a low blood oxygen saturation level, comprising coupling to said patient's vascular system an extracorporeal blood circulation path, comprising apparatus for oxygenating blood flowing therein and withdrawing $CO_2$ therefrom, and adjusting the flow rate of blood flowing in said extracorporeal blood circulation path to not exceed flow rate of 30 ml/kg per minute. The patient is able to breathe spontaneously. Alternatively, the patient is mechanically ventilated. The support to the patient may be provided as an auxiliary system instead of an ECMO.

Yet, in a further aspect, this invention provides a system for automatic priming of at least one cannula, comprising at least: a) a priming cap including an inlet and an outlet that are sealed from each other when mounted on a cannula; b) a saline repository; c) a priming pump comprising a drive unit and a replaceable priming pump head; d) a fluid path comprising sterile tubing between a first lumen and second lumen of the at least one cannula, said fluid path not including the priming cap; wherein the priming cap is removably fittable over the first and second lumens, such that, when the priming cap is fitted over the first and second lumens, the inlet is in fluid communication with the first lumen of the at least one cannula, and the outlet is in fluid communication with the second lumen of the at least one cannula, such that the at least one cannula, priming cap, saline repository, priming pump head, and fluid path form a closed loop for fluid flow, and when the priming cap is not fitted over the at least one cannula, the at least one cannula is insertable into a patient vascular system; and e) a controller configured to operate the priming pump when the priming cap is fitted over the at least one cannula, and thereby evacuate air from the closed loop. In some optional implementation of the system. The at least one cannula, the priming cap, the saline repository, the priming pump head, and the fluid path are contained within a cartridge, wherein the cartridge is attachable to and removable from a base containing the controller. The controller is configured to commence a priming operation automatically upon attachment of the cartridge to the base. The system may further comprise a sterile patient penetration kit, that includes an introducer, one or more dilators, and a guidewire to allow cannulation of the patient. In some embodiments, the controller is configured to operate the priming pump while the sterile patient penetration kit remains hermetically sealed.

In some other optional embodiments, the fluid path further comprises an oxygenation system.

Optionally, the first and second lumens of the cannula comprise a drainage lumen and an infusion lumen, and, when the at least one cannula is inserted into a patient vascular system, the oxygenation system is configured to oxygenate blood withdrawn via the drainage lumen and return oxygenated blood via the infusion lumen. As mentioned above, the system may operate with single lumen cannulas or with a dual lumen cannula.

Alternatively, the closed loop comprises, in order, the first lumen, the fluid path, the second lumen, an inlet of the priming cap, the saline repository, the priming pump head, the outlet of the priming cap, and again the first lumen.

In a further aspect of this invention, a system for extracorporeal oxygenation of blood is provided, the system comprising: a) a reusable base comprising at least: a controller; one or more pump drive units; and one or more pump motor; and b) a single-use cartridge comprising: one or more pump head, each pump head controllable by a respective pump drive unit and motor when the cartridge is installed in the base; an oxygenator; at least one cannula, said at least one cannula including a drainage lumen for removing deoxygenated blood from a patient vascular system, and an infusion lumen for returning oxygenated blood to the patient vascular system; and sterile tubing configured to deliver deoxygenated blood from the drainage lumen to the oxygenator, and to deliver oxygenated blood from the oxygenator to the infusion lumen; wherein, when the cartridge is installed in the base, the controller is configured to pump blood from the patient vascular system through a sterile flow path defined by the at least one cannula, sterile tubing, one or more pump heads, and oxygenator, and to oxygenate said pumped blood. The one or more pump drive units of the system may include a priming pump drive unit, and further comprising, within the single-use cartridge, a priming cap including an inlet and an outlet that are sealed from each other, a saline repository, and a priming pump head controllable with the priming pump drive unit; wherein the priming cap is removably fittable over the at least one cannula, such that, when the priming cap is fitted over the at least one cannula, the inlet is in fluid communication with a first lumen of the at least one cannula, and the outlet is in fluid communication with a second lumen of the at least one cannula, such that the at least one cannula, priming cap, saline repository, priming pump head, sterile tubing, and oxygenator form a closed loop for fluid flow, and when the priming cap is not fitted over the at least one cannula, the at least one cannula is insertable into a patient vascular system; and wherein the controller is configured to operate the priming pump when the priming cap is fitted over the at least one cannula, and thereby evacuate air from the closed loop.

In additional aspect, the invention is directed to a method of increasing blood oxygenation level and $CO_2$ removal in a patient capable of spontaneous breathing, the method comprising: introducing a first cannula into a first blood vessel for draining blood therefrom, and a second cannula into a second blood vessel for infusing oxygenated blood thereto, the first and second cannulas being linked to an extracorporeal blood-oxygenation system through a first flow line and a second flow line, respectively, and circulating said patient's blood at a circulation rate of no more than about 30 ml/kg per minute through said extracorporeal blood-oxygenation system to oxygenate said blood and obtain $CO_2$ removal from the blood and an increase in blood oxygenation level of the patient. Optionally, the method is further comprising determining at least one of (i) blood circulation rate and (ii) size of cannula(s), said determination being based on the patient's weight. The determining comprises: a) determining the blood circulation rate based on the patient's weight and a desired target blood oxygenation level and $CO_2$ removal; and b) determining the size of cannula suitable for said patient based on the desired blood circulation rate.

Yet, this invention is directed to a method of increasing blood oxygenation level and CO2 removal in a conscious patient capable of spontaneous breathing, the method comprising: introducing a dual-lumen cannula into a blood vessel of said patient, said dual-lumen cannula comprising a drainage tube for draining deoxygenated blood from the blood vessel and an infusion tube for infusing oxygenated blood into the blood vessel, the drainage tube and the infusion tube being linked to an extracorporeal blood-oxygenation system through a first flow line for said draining and a second flow line for said infusing, and circulating said patient's blood at a circulation rate of no more than about 30 ml/kg per minute through said extracorporeal blood-oxygenation system to oxygenate said blood and obtain $CO_2$ removal from the blood and an increase in blood oxygenation level of the patient. In some optional implementations of this method, a dual lumen cannula comprising an external tube that envelops an internal tube is provided. In this optional scenario, one of the external and internal tubes being the drainage tube and the other being the infusion tube. Alternatively, the drainage tube and the infusion tube may be arranged side-by-side in the dual lumen cannula used. Optionally, the method is further comprising monitoring the blood oxygenation parameters of the patient during treatment.

The following studies have been carried out on 200 lbs/90 kg Large-White X Landrace swine models. Swine is considered one of the major animal species used in translational research, surgical models, and procedural training, mainly to share similar anatomic and physiologic characteristics of humans. All swine models used in the following studies underwent individual veterinary examinations, including blood tests (CBC) at the LAHAV C.R.O. laboratory, according to the facility SOPs. The blood tests, together with the general physical examination performed prior to the beginning of the studies, reflected the health status of the swine models, enabling the determination of the suitability of each animal to the study.

A direct oxygenation device was connected in a vein-to-vein connection to swine models to allow extracorporeal oxygenation of the swine's blood in closed circulation. The system's oxygenator included two compartments connected through a semipermeable membrane partition. Delivering blood through one compartment and oxygen through the other facilitated the exchange of oxygen into the blood through the semi-permeable membrane partition. The blood compartment of the oxygenator was connected to the veins by ⅜" tubes connected to cannulas placed in the femoral vein and jugular vein alike or alternatively to a dual lumen cannula in the internal jugular vein. The second compartment of the oxygenator was connected to a standard oxygen supply source. The system pumped blood from the swine's vascular system, oxygenated it, and then returned it into the vascular system, thus elevating oxygen saturation levels and providing respiratory support to the swine models.

The swine models used in the studies were induced into a state of hypoxemia. The oxygen gas concentration was lowered (using nitrous), mimicking a state of Respiratory Failure of compromised sick lungs. This was achieved by mixing pure oxygen with medical air and $N_2O$ to reduce the oxygen concentration levels to ~15%, thus reducing the oxygen saturation levels of the swine models to ~85% and below, with each swine model responding independently.

Swines were anesthetized however maintained breathing and connected to all relevant instruments according to the facilities' SOPs. An endotracheal tube was connected to a gas mixer of medical oxygen and nitrogen to control the oxygen concentration. Swan Ganz catheter (used to monitor blood flow and pressures in and around the heart) was positioned by using angiography and allowed taking blood samples from the Pulmonary artery as close as possible to the catheter. Monitor equipment was set up (for continuous recordation of vital signs), and Arterial Blood Gas (ABG) was tested and calibrated. The swine models were sedated, with vital signs being continuously monitored.

The following access points were installed for phlebotomy (for blood withdrawal): Pulmonary Artery, Carotid Artery, Femoral Vein.

The inlet tube was used for circulating blood drained from the body to the oxygenator, while the outlet tube was used for circulating the oxygenated blood from the oxygenator back to the body. The inlet tube was connected to the cannula inserted into the femoral vein, with the outlet tube connected to the cannula inserted into the jugular vein. For studies performed with a dual lumen cannula inserted into the jugular vein, both the inlet and outlet tubes were connected to the corresponding connections.

The system was circulated with saline (~1000 ml) prior to attachment to the cannulas. The cannula tubes were connected to the ⅜" diameter inlet and outlet tubes of the system, and the oxygen source was connected with 8 mm tube to the system's oxygenator oxygen inlet, with oxygen flow rate set to 3 L/min. The oxygenator gas outlet was left open during the experiments.

This process was performed and validated by the LAHAV C.R.O. medical teams. This was achieved by mixing pure oxygen with medical air and N2O to reduce the oxygen concentration levels to ~15%, thus reducing the oxygen saturation levels of the swine models to ~85% and below, with each swine model responding independently.

For blood sampling, both before and after the system's oxygenator, ⅜"×⅜" T-connectors were used to connect to two-way stopcocks, which allow for taking the blood samples. Blood was sampled from 4 Test Points (TPs):

TP1—Femoral vein (femoral venous blood before oxygenation process)
TP2—Oxygenator outlet ("after", venous blood after oxygenation and before mixing with jugular venous blood)
TP3—Pulmonary artery (PA, filled with vena cava blood after extracorporeal oxygenation, after mixing with jugular venous deoxygenated blood, and before entering the lungs for oxygenation process)
TP4—Carotid artery (oxygenated blood after the lungs)
Study 1—Femoral-Jugular Study
Part 1—

The objective of this study was to show that 1 L/min blood flow is sufficient to support a patient in a state of hypoxemia; targeting to increase $O_2$ saturation from <85% to ~95%. 200 lbs/90 kg swine were used for this study, using 2 large commercial 18 Fr cannulas (Medtronic): the first cannula inserted into the Jugular vein and the second cannula connected to the Femoral vein. The insertion process required a surgical insertion using a radiographic procedure due to the dimensions and length of the cannula passing through the right atrium of the heart. The blood flow rate through the extracorporeal oxygenation system was 1-1.5 L/min blood flow, with an oxygen flow rate of 3 L/min and low oxygen ventilation support (<20% $O_2$ gas concentration).

Data was collected and analyzed to assess the minimal blood flow required to elevate and stabilize oxygen saturation levels. The results are provided in Table 1.

TABLE 1

Saturation level results for Study 1 - Part 1

| Cycle | $O_2$ gas concentration | Blood flow rate (L/min) | Pre-system activation (off) | After system activation (on) |
|---|---|---|---|---|
| 1 | 15% | 1 | 74% | 90% |
| 2 | | | 80% | 91% |
| 3 | | | 78% | 92% |
| 4 | | | 79% | 92% |
| 5 | | 1.5 | 76% | 93% |
| 6 | | 1 | 77% | 96% |
| 7 | 18% | | 88% | 95% |
| 8 | | | 88% | 95% |

As seen, the method is capable of elevating oxygen saturation levels from values even below 80%, which are conditions typically defined for patients as critically ill (in which patients are typically placed on mechanical ventilation or ECMO systems).

Part 2—

The objective of this study was to assess oxygenation with different blood flow rates. The $pO_2$ levels of the swine were stabilized to 100-120 mmHg, and the blood flow rate was investigated to assess the minimum flow levels that would add a minimum of 10 mmHg to blood oxygen. All parameters expected for blood flow levels were the same as in Part 1 above. The results are provided in Table 2.

TABLE 2

Saturation level results for Study 1 - Part 2

| Blood flow rate (L/min) | Pre-system activation (off) | After system activation (on) |
|---|---|---|
| 1 | 88% | 92% |
| 1 | 85% | 93% |
| 2 | 78% | 99% |
| 1 | 77% | 91% |

The system and method that were used successfully enabled elevating oxygen saturation levels similar to Part 1 of the study.

Study 2—Dual Lumen Jugular-Jugular Study

The objective of this study was to examine the feasibility of blood oxygenation and $CO_2$ removal by using a commercial dual lumen cannula inserted into the internal jugular vein.

200 lbs/90 kg swine were used for this study, using dual lumen commercial 23 Fr cannula (Maquet Avalon). The insertion process required a surgical insertion using a radiographic procedure due to the complexity in the correct positioning of the cannula. The blood flow rate through the extracorporeal oxygenation system was 1-1.5 L/min blood flow, with an oxygen flow rate of 3 L/min and low oxygen ventilation support (16% $O_2$ gas concentration).

The results are provided in Table 3.

TABLE 3

Saturation level results for Study 2

| Blood flow rate (L/min) | Pre-system activation (off) | After system activation (on) |
|---|---|---|
| 1 | 87% | 95% |
| 1 | 86% | 95% |
| 1.5 | 83% | 97% |

By using the extracorporeal oxygenation system of the invention and methods described herein, the oxygen saturation levels were elevated from ~80% to target levels above 95%.

Study 3—Small-Scale Dual Lumen Juglar-Juglar Study

The objective of this study was to examine the feasibility of blood oxygenation and $CO_2$ removal by using a small-scale dual lumen inserted into the internal jugular vein without the need for radiographic-guided insertion. 200 lbs/90 kg swine were used for this study, using dual lumen commercial 18 Fr small-scale cannula (according to the present disclosure). No radiographic imaging (or other types of imaging) was required for the positioning of the cannula. The blood flow rate through the extracorporeal oxygenation system was 1-1.5 L/min blood flow, with an oxygen flow rate of 3 L/min and low oxygen ventilation support (14.5% $O_2$ gas concentration).

The small-scale dual lumen cannula allowed simultaneous venous drainage and reinfusion of blood via the internal jugular vein. The extracorporeal oxygenation system included a centrifugal pump activated to pump blood from the 'swine's right internal jugular vein through the cannula's outlet drainage tube. The blood was circulated through the system's oxygenator, providing the blood with an enriched oxygen content and depleted $CO_2$ levels. In a closed system, the oxygenated blood was circulated back through the cannula's inlet reinfusion tube.

The swine model was placed into a state of hypoxemia achieved by mixing $N_2O$ and oxygen in a mixture for ventilation in different concentrations to reach the targeted oxygen saturation level. Swine model oxygen saturation was monitored and stabilized at levels of ~85%. Blood sampling was carried out both before and after the system's oxygenator at:

TP1—Femoral vein (femoral venous blood before oxygenation process)

TP2—Oxygenator outlet ("after", venous blood after oxygenation and before mixing with jugular venous blood)

TP3—Pulmonary artery (PA, filled with vena cava blood after extracorporeal oxygenation, after mixing with jugular venous deoxygenated blood & before entering the lungs for oxygenation process)

TP4—Carotid artery (oxygenated blood after the lungs)

As the swine model was in a state of hypoxemia, the monitor saturation level illustrated deteriorated blood oxygen saturation levels.

With the activation of the system, the swine's blood was drawn from and returned to the right jugular vein using the small-scale dual lumen cannula. The swine model's oxygen saturation was monitored at several intervals with blood sampling taken from the testing points.

The results are provided in Table 4.

TABLE 4

Saturation level results for Study 3

| SpO$_2$ | | PaO$_2$ | | PaCO$_2$ | | pH | |
|---|---|---|---|---|---|---|---|
| Off | On | Off | On | Off | On | Off | on |
| 86% | 97% | 50 | 64 | 31 | 26 | 7.53 | 7.6 |
| 85% | 95% | 50 | 65 | 27 | 26 | 7.6 | 7.62 |
| 88% | 96% | 53 | 72 | 29 | 25 | 7.58 | 7.62 |
| 89% | 93% | 57 | 58 | 28 | 25 | 7.57 | 7.63 |
| 85% | 94% | 46 | 65 | 26 | 23 | 7.59 | 7.62 |
| 85% | 95% | 47 | 66 | 26 | 23 | 7.57 | 7.62 |
| 87% | 96% | 52 | 68 | 40 | 33 | 7.46 | 7.51 |
| 88% | 96% | 53 | 71 | 35 | 31 | 7.49 | 7.53 |

As can be seen from Table 4, a low blood flow of 1-1.5 L/min using the small-scale dual-lumen cannula resulted in saturation levels of 95-96%. No Radiographic guidance was used in the insertion process. Further, the increase in monitor saturation levels was in parallel with the increase in arterial pO$_2$, indicating high oxygenation ability in low blood flow rate and low oxygen concentration. The small-scale dual-lumen cannula was inserted and removed without complications; after removing the cannula from the swine's jugular vein, no signs of blood clots or fatigue were observed.

Tables 5-1 and 5-2 shows the aggregated results of Studies 1-3.

TABLE 5-1

Aggregated results

| | Small-scale dual lumen cannula (Jugular-Jugular) | | 23Fr dual-lumen cannula (Jugular-Jugular) | | 18Fr cannulas (Femoral-Jugular) | |
|---|---|---|---|---|---|---|
| Oxygen concentration | 14. % | | 16% | | 17.6% | |
| Average monitor saturation | 1 L/min 96% | 1.5 L/min 95% | 1 L/min 95% | 1.5 L/min 97% | 1 L/min 95.5% | 1.5 L/min 96.5% |
| Increase in arterial pO$_2$ (mmHg) | 16-18 | | 1 L/min 8-17 | 1.5 L/min 32 | 8-18 | |

TABLE 5-2

Aggregated results

| | SpO$_2$ | | PaO$_2$ | | PaCO$_2$ | | pH | |
|---|---|---|---|---|---|---|---|---|
| Cannula type | Off | On | Off | On | Off | On | Off | On |
| Small-scale dual-lumen (jug.-jug.) | 86% | 97% | 50 | 64 | 31 | 26 | 7.53 | 7.6 |
| | 85% | 95% | 50 | 65 | 27 | 26 | 7.6 | 7.62 |
| | 88% | 96% | 53 | 72 | 29 | 25 | 7.58 | 7.62 |
| | 89% | 93% | 57 | 58 | 28 | 25 | 7.57 | 7.63 |
| | 85% | 94% | 46 | 65 | 26 | 23 | 7.59 | 7.62 |
| | 85% | 95% | 47 | 66 | 26 | 23 | 7.57 | 7.62 |
| | 87% | 96% | 52 | 68 | 40 | 33 | 7.46 | 7.51 |
| | 88% | 96% | 53 | 71 | 35 | 31 | 7.49 | 7.53 |
| 23Fr dual lumen (jug.-jug.) | 87% | 95% | 52 | 61 | 37 | 30 | 7.48 | 7.56 |
| | 86% | 95% | 46 | 63 | 36 | 31 | 7.49 | 7.55 |
| | 83% | 97% | 47 | 79 | 34 | 30 | 7.52 | 7.57 |
| 18Fr cannulas (fem.-jug.) | 88% | 95% | 61 | 73 | 29 | 23 | 7.59 | 7.64 |
| | 88% | 95% | 54 | 61 | 27 | 23 | 7.6 | 7.65 |
| | 83% | 95% | 49 | 67 | 41 | 31 | 7.42 | 7.51 |

TABLE 5-2-continued

Aggregated results

| | SpO$_2$ | | PaO$_2$ | | PaCO$_2$ | | pH | |
|---|---|---|---|---|---|---|---|---|
| Cannula type | Off | On | Off | On | Off | On | Off | On |
| | 89% | 95% | 54 | 71 | 38 | 31 | 7.4 | 7.51 |
| | 83% | 96% | 58 | 68 | 37 | 29 | 7.47 | 7.56 |
| | 89% | 96% | 53 | 64 | 34 | 28 | 7.5 | 7.59 |

As can be seen from the results, the method of this disclosure provides safe and consistent oxygenation levels in spontaneously breathing swine, circulating only a portion (about a ⅕) volume of blood at relatively low blood flow rates. Utilizing also small scale dual-lumen cannula enabled obtaining significantly less invasive and less complicated procedure without requiring any imaging techniques to guide the cannula into position.

The present disclosure, in some embodiments, concerns a system for a cannula and sterile tubing connected thereto, and more specifically, but not exclusively, to an auto-priming system that is integrated into an extracorporeal oxygenation system.

Reference is now made to the drawings:

FIG. 1A is a schematic isometric front view illustration of an extracorporeal oxygenation system 100, having a reusable base 110 and a disposable cartridge 10 that is practically a plug and play single unit box containing all or most of the disposable components of system 100 that are being in contact with the patient's blood. Detailed description of these components will be provided hereinbelow with reference to FIGS. 2-3. These components are gathered and designed to replace the complicated multiple-step assembly and connection of these disposables to the extracorporeal oxygenation system with a more user-friendly, single step process, reducing the need for time and special training to configure the required disposables safely and correctly. In this drawing Cartridge 10 is positioned on top of base 110 ready to be plugged onto it.

Figure 1B:
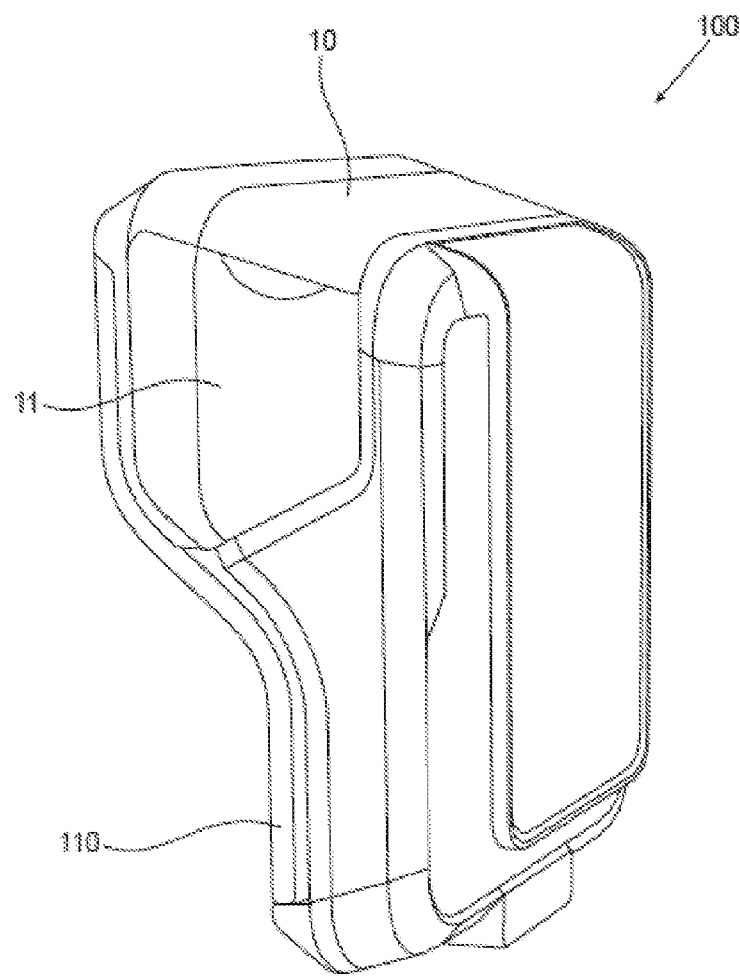
FIG. 1B is a schematic side view illustration of the extracorporeal system of FIG. 1A in a connected form according to embodiments of the present disclosure.

FIG. 1B is a schematic side view illustration of the extracorporeal system of FIG. 1A, wherein cartridge 10 and Base 110 are connected to each other according to some optional embodiments of the present disclosure. In this view, cover 11 is shown. Before usage of extracorporeal oxygenation system 100 cover 11 is being removed and a "window" allowing approach to the inner space and to the components of cartridge 10 is uncovered. This allows the operator to pull out a cannula, preferably but not necessarily, a primed cannula, and to connect the oxygenator 52 by a dedicated connector 52' to an oxygen supply (shown in FIG. 5A).

Figure 1C:
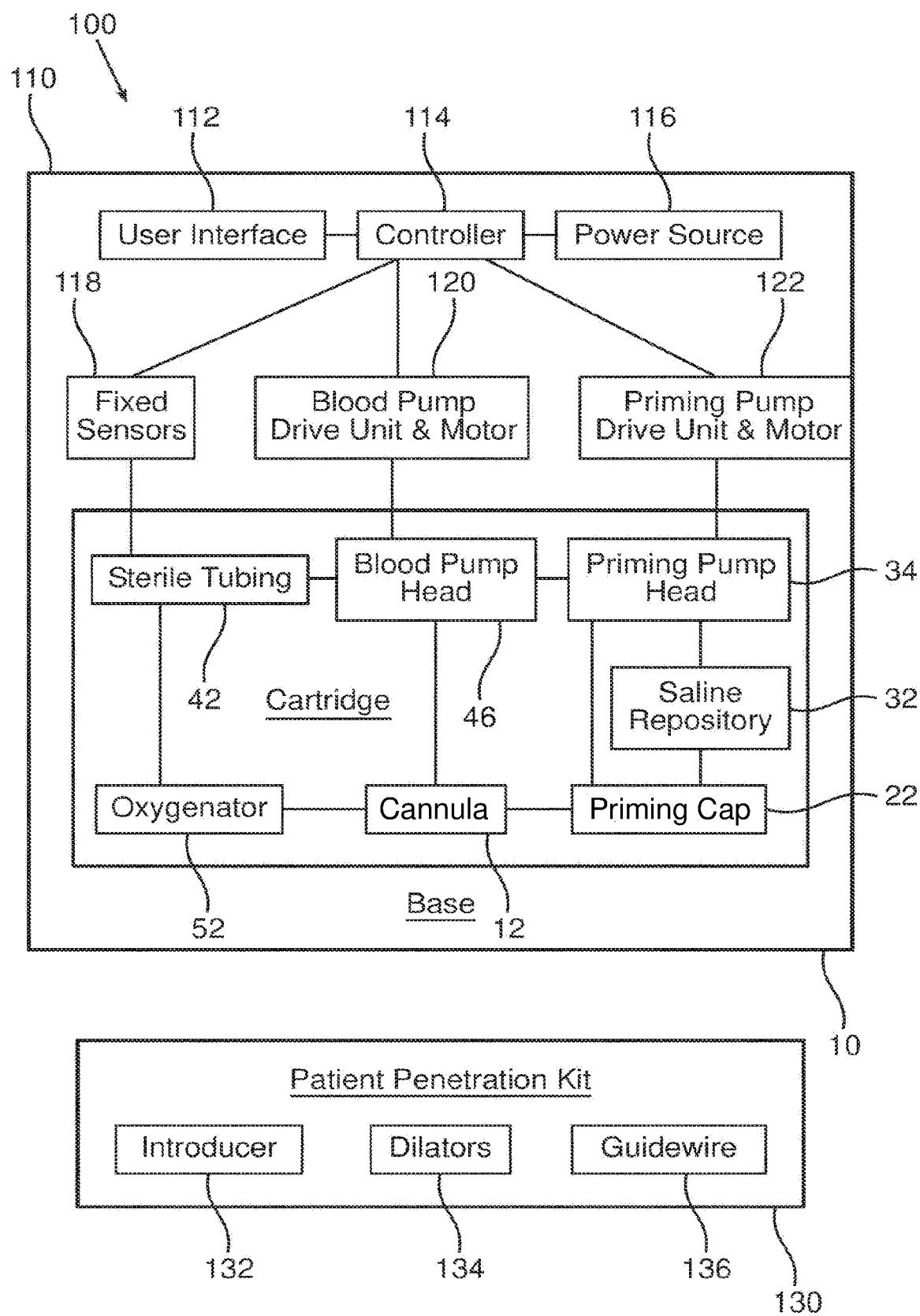
FIG. 1C is a schematic block diagram of an extracorporeal oxygenation machine including an auto-priming cartridge, according to embodiments of the present disclosure.

FIG. 1C is a schematic block diagram depicting major components of an extracorporeal oxygenation system 100 in accordance with some optional implementation of the invention. As used in the present disclosure, extracorporeal oxygenation systems are systems that drain blood through a blood vessel (e.g., a vein or an artery) using a pump, pass the blood through an external oxygenation system in order to reduce carbon dioxide ($CO_2$) levels and enrich the blood with oxygen, and infuse the oxygenated blood back into the patient's circulatory system. The extracorporeal oxygenation system may be, for example, an extracorporeal membrane oxygenation (ECMO) system. The extracorporeal oxygenation system may serve as a sole source of oxygenation for the 'patient's blood, or it may be used to supplement other sources of oxygen, such as a mechanical ventilator or the 'patient's independent breathing. In exemplary embodiments, system 100 is designed for use as a supplemental oxygenator for a patient that is conscious and capable of breathing independently, albeit with reduced efficacy.

System 100 is comprised of a reusable base 110, a single-use cartridge 10 that is connectable to base 110, and patient penetration kit 130.

The reusable base 110 includes a user interface 112. User interface 112 may include a keyboard, a touch screen, or any other mechanism for receiving user inputs. User interface 112 also includes a display for displaying parameters relevant to the functioning of system 100. The user inputs and display parameters may relate to the function of any of the components of system 100, for example, the flow rate of blood through system 100, pressure of blood at different points within system 100, temperature of blood, and target oxygenation level of blood flowing through system 100.

Base 110 further includes a programmable logic controller 114. Controller 114 may include a processing circuitry that executes software that includes instructions for performing a method according to embodiments of the present disclosure. The processing circuitry may include a computer readable storage medium having computer readable program instructions thereon for causing a processor to carry out aspects of the system according to the present disclosure.

Base 110 further includes power source 116. Power source 116 may be a power cord that is connectable to a power grid. In addition, or in the alternative, power source 116 may be a battery, for example, a rechargeable battery. Power source 116 provides power to the controller as well as to the pump motors and drive units 120, 122 described further herein.

Base 110 further includes one or more fixed sensors 118. Fixed sensors 118 may include, for example, an optical analyzer for measuring parameters such as hematocrit percentage, oxygen saturation, hemoglobin, and blood temperature. Fixed sensors 118 may also include a flow meter. The fixed sensors 118 may analyze these parameters of the blood while the blood is in sterile tubing Base 110 also includes a blood pump drive unit and motor 120, and a priming pump drive unit and motor 122. The functions of the blood pump and the priming pump will be described further herein. Each pump drive unit and motor 120, 122 includes a driver and a motor. The driver is an electronic unit (e.g., a printed circuit board assembly) that receives input signals (e.g., analog signals) for controlling the motor. The motor receives power from the power source 116. The magnet of the magnetic motor controls, through magnetic force, a magnetic impeller that is part of a disposable pump head within cartridge 10. In addition, in exemplary embodiments, the priming pump is a peristaltic pump. The pump heads are connectable to disposable sterile tubing that is part of cartridge 10, for effecting pressure on one or more fluid flow lines within cartridge 10.

Base 110 may be installed within a hospital room, for example, mounted on a wall mount. Alternatively, base 110 may be portable. For example, base 110 may be situated on a rolling cart or within an ambulance. The hospital room, rolling cart, or ambulance may include equipment for use in conjunction with system 100, for example, one or more oxygen canisters, a backup power pack, an uninterrupted power supply (UPS), or a blood heater.

Still referring to FIG. 1C, system 100 further includes cartridge 10. Cartridge 10 is a disposable cartridge that is designed to be removed from, and inserted into, the base 110. In general, cartridge 10 includes components that come into contact with a 'patient's blood and thus are replaced between each patient use. Cartridge 10 includes a cannula 12 priming cap 22, and saline repository 32, the functions of which will be described further herein. Cartridge 10 also includes priming pump head 34, which is controlled by the priming pump motor in base 110, and blood pump head 46, which is controlled by the blood pump motor in base 110. Cartridge 10 further includes sterile tubing through which fluids flow, and around which the fixed sensors 118 may be applied, and oxygenator 52 for oxygenating blood flowing through the cartridge.

System 100 further includes a patient penetration kit 130. Patient penetration kit 130 includes standard materials that are used to insert a cannula into a patient vascular system. These materials include, for example, an introducer 132, which may include a needle or trocar; one or more dilators or expanders 134, and a guidewire 136. Patient penetration kit 130 may be stored separately from the cartridge 10.

Figure 2:
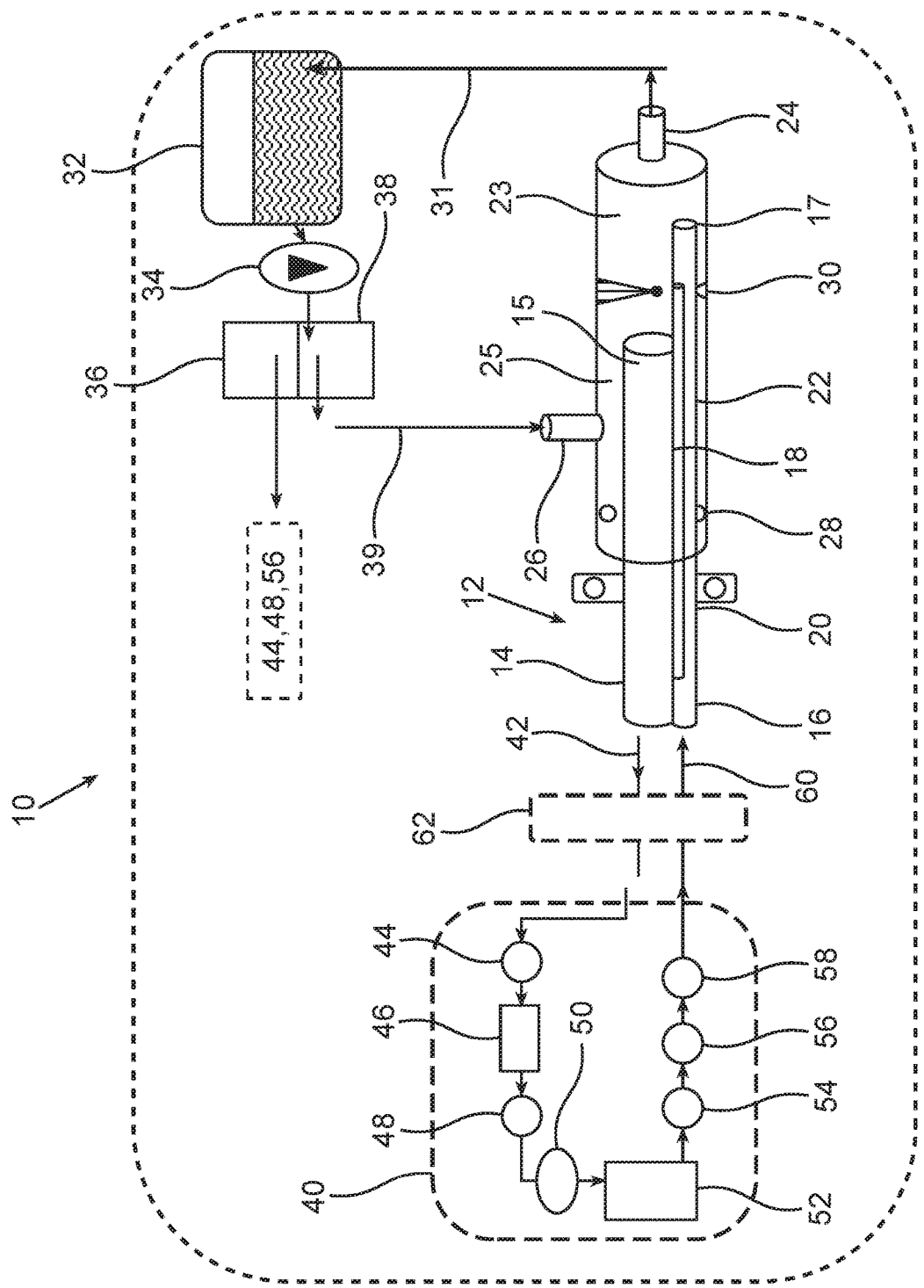
FIG. 2 is a schematic block drawing of components of the auto-priming cartridge from the extracorporeal oxygenation machine of FIG. 1B, according to embodiments of the present disclosure.
Figure 3:
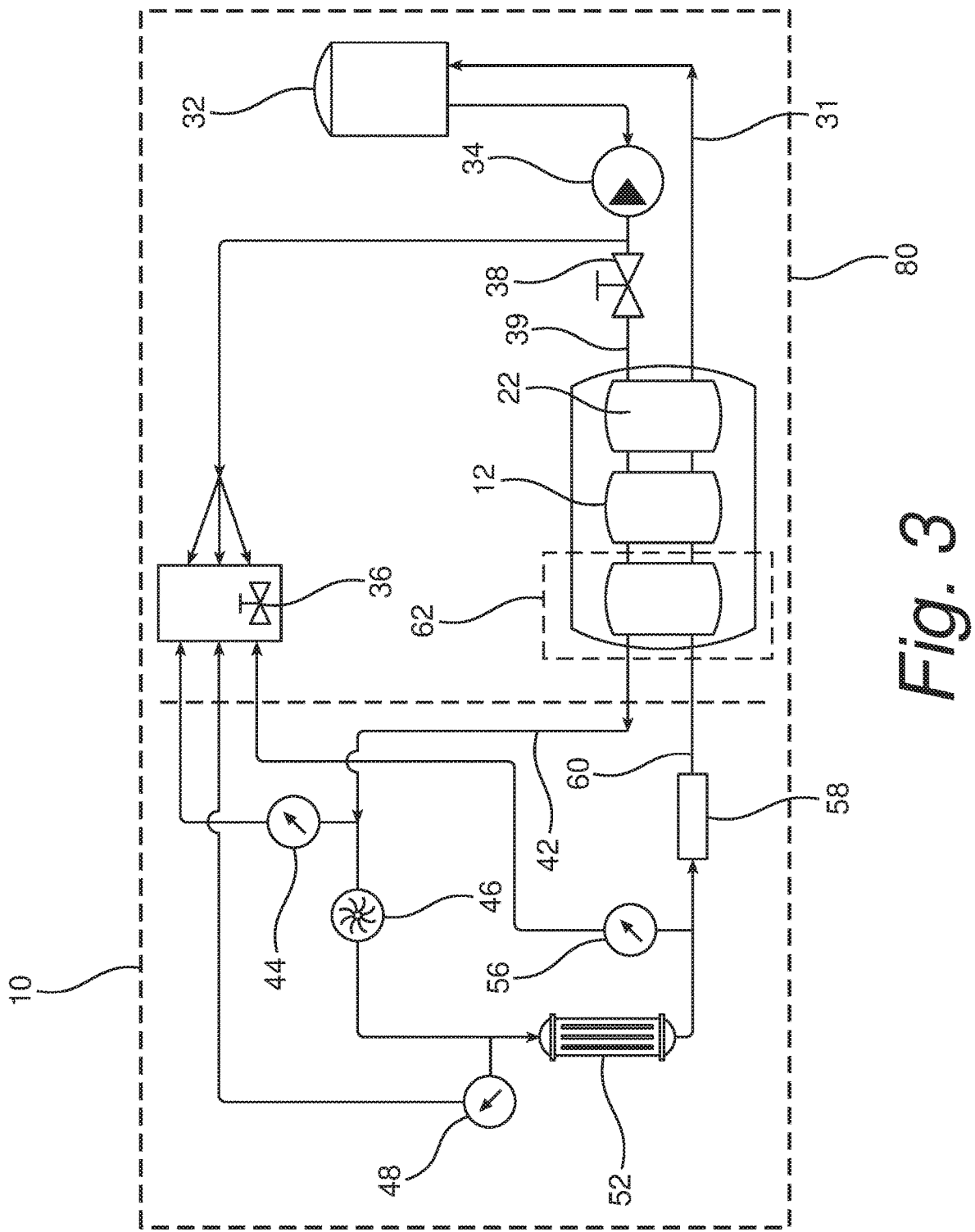
FIG. 3 is a schematic block drawing of the auto-priming cartridge of FIG. 2, showing in particular paths of fluid flow during a priming operation, according to embodiments of the present disclosure.

FIGS. 2 and 3 contain schematic diagrams illustrating the components and functioning of cartridge 10.

In the configuration of FIGS. 2 and 3, cartridge 10 is illustrated in a position in which a fluid path for a cannula 12 is ready to be primed by infusion of saline. In this position, a priming cap 22 is fitted over a cannula 12, such that the priming cap 22, cannula 12, and other components form a closed loop for infusion of saline. When priming cap 22 is removed and the cannula 12 is inserted into the body, the same closed loop is used for transfer of blood between the patient vascular system and an oxygenation module 40 contained within cartridge 10. During the priming process, cartridge 10 is enclosed in a sterile enclosure, which may be made of any suitable material. The sterile enclosure may remain sealed until after the priming is complete and the cannula is ready to be inserted into the 'patient's body.

Referring to FIG. 2, cartridge 10 includes cannula 12. In exemplary embodiments, cannula 12 is a dual lumen cannula having two lumens arranged side-by-side. Dual lumen cannula 12 includes a first lumen 14 having end 15, and a second lumen 16 having end 17. In exemplary embodiments, the first lumen 14 is a drainage lumen, such that end 15 is an inlet, and the second lumen 16 is an infusion lumen, such that end 17 is an outlet. The drainage lumen 14 is used to withdraw deoxygenated blood from the patient's vascular system into cartridge 10, and the infusion lumen 16 is used to deliver oxygenated blood from cartridge 10 into the patient's vascular system. An extent of infusion lumen 16 is greater than an extent of drainage lumen 14. The uneven extent of the lumens 14, 16 allows different regions of a priming cap 22 to be affixed to the ends 15, 17 of the lumens 14, 16, as will be described further herein.

In some optional embodiments, the dual lumen cannula comprises an external tube that envelops an internal tube, one of the external and internal tubes being a drainage tube and the other being an infusion tube. By some such embodiments, the external tube drains deoxygenated blood from the blood vessel, and the internal tube infuses oxygenated and $CO_2$-poor blood into the blood vessel. In other embodiments, the internal tube drains deoxygenated blood from the blood vessel, and the external tube infuses oxygenated blood into the blood vessel. In the side-by-side configuration, one tube is used for drainage of deoxygenated blood from the blood vessel, and the other tube infuses oxygenated and CO2-poor blood into the blood vessel.

In other embodiments, the drainage tube and the infusion tube are arranged side by side in said dual lumen cannula.

In the specific example illustrated herein, dual lumen cannula 12 further includes a guidewire sheath 18 having an entrance 19 (not shown). When the cannula 12 is inserted into the 'patient's body, the cannula 12 is threaded along guidewire 136 via sheath 18.

Cannula 12 further includes wings 20. Wings 20 may be attached to a 'patient's body, for example, with stitches, to ensure that the cannula 12 remains in place during an oxygenation procedure.

Priming cap 22 is removably fittable over the ends 15, 17 of the first and second lumens 14, 16. Priming cap 22 includes two regions: region 23, which is fluidically connected to outlet 17 of lumen 16, leading to outlet 24 of the priming cap 22; and region 25, which is fluidically connected to an inlet 15 of lumen 14, and which receives fluid through inlet 26 of the priming cap 22. Regions 23, 25 are demarcated by internal seals 28, 30, which may be, for example, O-rings. When fluid enters priming cap 22 via inlet 26, the fluid fills the entire region 25 between seal 28 and seal 30. When fluid enters priming cap 22 via an outlet of lumen 16, the fluid fills the entire region 23 between seal 30 and the outlet 24 of the priming cap 22. The locations and orientations of outlet 24 and inlet 26 within their respective regions 23, 25 are merely exemplary, and other locations and orientations are also feasible. In addition, while, in the illustrated embodiment, cannula 12 is a dual lumen cannula, in alternative embodiments, cannula 12 comprises two separate cannulas, one used for drainage, and one used for infusion. In such embodiments, there may be a separate priming cap 22 for each cannula, or the priming cap 22 may be split into two branches, namely an inlet branch and an outlet branch.

Cartridge 10 further includes saline repository 32, which is connected via tubing 31 to outlet 24 of the priming cap 22. Saline repository 32 is connected to disposable pump head 34 of a priming pump, whose drive unit is part of base 10, as discussed above. In exemplary embodiments, the priming pump (including the drive unit 122 contained in the base 10) has a small dimension of up to 10 cm in length, and up to 2 kg weight. In exemplary embodiments, the priming pump is a peristaltic pump, such that the priming pump head 34 fits around sterile tubing carrying saline from the saline repository 32. A peristaltic pump is relatively low-cost and has a simple interface with the disposable sterile tubes carrying the saline.

From the priming pump head 34, the fluid path proceeds to two valves: pressure meter valve 36, and blood path valve 38. The pressure meter valve 36 and blood path valve 38 may be separately controlled, such that pressure meter valve 36 is open and blood path valve 38 is closed, or vice versa. Pressure meter valve 36 is connected to three pressure meters 44, 48, 56. This connection is represented schematically in FIG. 2 and is further shown in FIG. 3 with the fluid lines connecting between pressure meter valve 36 and the respective pressure meters. When pressure meter valve 36 is open, fluid (e.g. saline) flows between pump head 34 and the pressure meters 44, 48, 56. Pressure meter valve 36 is separately controllable to permit flow of saline to any one of the pressure meters 44, 48, 56. During a priming process, once fluid fills the lines between pressure meter valve 36 and the pressure meters 44, 48, 56, the pressure meter valve 36 may be closed. When blood path valve 38 is open, fluid (e.g., saline) flows between pump head 34, via tubing 39, to the inlet 26 of priming cap 22, so that the fluid may continue to prime areas where blood will flow, following insertion of cannula 12 into a patient vascular system.

After fluid enters inlet 26 of priming cap 22, fluid fills region 25 of priming cap 22, and enters the drainage lumen 14 of cannula 12 at inlet 15. From the drainage lumen 14, fluid proceeds via tubing 42 through or adjacent to pressure meter 44.

Pressure meter 44 is preferably but not necessarily a membrane pressure sensor, with saline on one side of the membrane (from pressure meter valve 36) and fluid from the blood path on the other side of the membrane. The sensor is configured to indicate (e.g., to a controller) when a pressure differential across the membrane changes. When the cannula 12 is inserted into the patient vascular system, pressure meter 44 is used to verify that blood is flowing properly from the vein, i.e., that the vein has not collapsed.

Following pressure meter 44, the fluid passes through blood pump head 46. Blood pump head 46 may include a magnetic impeller that may be controlled by a centrifugal magnetic motor in blood pump drive unit 120 in base 110. The blood pump is used to adjust the pressure of fluid entering the oxygenator 52 so that the blood flows through the oxygenator at a desired rate.

Prior to entering oxygenator 52, the fluid passes through or adjacent to a second pressure sensor 48. After exiting oxygenator 52, the fluid passes through or adjacent to a third pressure sensor 56. The pressure sensors 48, 56 may be membrane pressure sensor, similar to pressure sensor 44. Pressure sensors 48 and 56 are used to evaluate the efficacy of the oxygenator 52. The oxygenator 52 may become clogged with blood over the course of its use. As a result, blood flows more slowly out of oxygenator 52 than into the oxygenator 52, and a pressure gradient may develop across the oxygenator 52. The pressures at pressure sensors 48 and 56 may be used to detect the presence of such a pressure gradient, and thus may be used to determine whether the cartridge 10 needs to be replaced.

Prior to entering oxygenator 52, blood also optionally passes through analyzer 50. As discussed above in connection with FIG. 1, analyzer 50 is part of the group of fixed sensors 118, and thus is technically part of base 110. The tubing of cartridge 10 passes through analyzer 50, such that the analyzer 50 itself does not contact the fluid. Analyzer 50 may measure oxygen saturation. Analyzer 50 may be, for example, an optical analyzer or an ultrasound analyzer.

The blood is then oxygenated at the oxygenator 52. Oxygenator 52 is connected to an oxygen input via connector 52', and releases carbon dioxide as a byproduct.

Following oxygenation at the oxygenator 52, fluid passes through temperature sensor 54. Temperature sensor 54 may include a metallic strip installed within the sterile tubes. If the temperature sensor 54 indicates that the blood temperature has cooled beyond a level suitable for reinfusion into a patient, a blood heater (not part of cartridge 10) may be used to reheat the blood if necessary. The fluid further passes through flow meter 58, before returning through sterile tubes 60 back to infusion lumen 16 of cannula 12. Flow meter 58 may be an ultrasonic meter that is part of the base 10. The flow meter is used to verify that the output of the blood pump, which operates based on revolutions per minute, translates into a desired flow, measured in liters per minute.

Sterile tubing 42, 60 may be comparatively long relative to the other components shown in cartridge 10. In exemplary embodiments, sterile tubing 42, 60 includes extended tubing 62, illustrated schematically in FIG. 2. Extended tubing 62 may be, for example, 1.2 meters long.

In view of the foregoing description, it is apparent that, when the priming cap 22 is fitted over the cannula 12 as shown in FIG. 2, cartridge 10 includes a closed loop for fluid flow. When the priming pump is activated, the priming pump head draws saline from saline repository 32. When blood pump valve 38 is open, the saline proceeds through blood pump valve 38, priming cap inlet 26, first lumen 14 (e.g., the drainage lumen), oxygenation module 40, second lumen 16 (e.g., the infusion lumen), priming cap outlet 22, and then back to saline repository 32. Throughout this process, air is expelled from the above-described fluid flow path and deposited into the saline repository 32. The expelled air remains in the saline repository 32, which is made of a material, such as a plastic, that is sufficiently expandable to accommodate the expelled air.

It is further apparent that, although in the illustrated embodiment, the closed loop is closed with an oxygenation module 40, any alternative fluid path between the first lumen 14 and second lumen 16 may be used. Thus, cartridge 10 may be used with a variety of systems that require priming and is not limited to oxygenation module.

In addition, it is further apparent that flow of fluid through this closed loop may proceed even when cartridge 10 remains sealed to ambient atmosphere. Thus, the cannula 12 and blood flow path may be primed while maintained in a sterile condition.

In summary, the extracorporeal blood oxygenation system of the invention is used to oxygenate blood of a patient. In one optional embodiment, cannula 12 is inserted at the 'patient's jugular vein. Blood flows out of the jugular vein, into the drainage lumen, and through tubing 42. Blood pump head 46 pumps the blood through oxygenator 52. The oxygenated blood is then returned through tube 60 and infusion lumen 16 back into the jugular vein. The cannula 12 may be inserted at any other suitable point, for example, at the superior vena cava. In addition, as discussed above, cannula 12 may include two separate cannulas, one for drainage and one for infusion.

Optionally, the blood oxygenation is performed while circulating the blood at a rate no greater than approximately 30 ml/kg per minute for external oxygenation for a patient that is conscious and capable of independent breathing, and for whom the oxygenation serves to supplement the patient's breathing.

Figure 4:
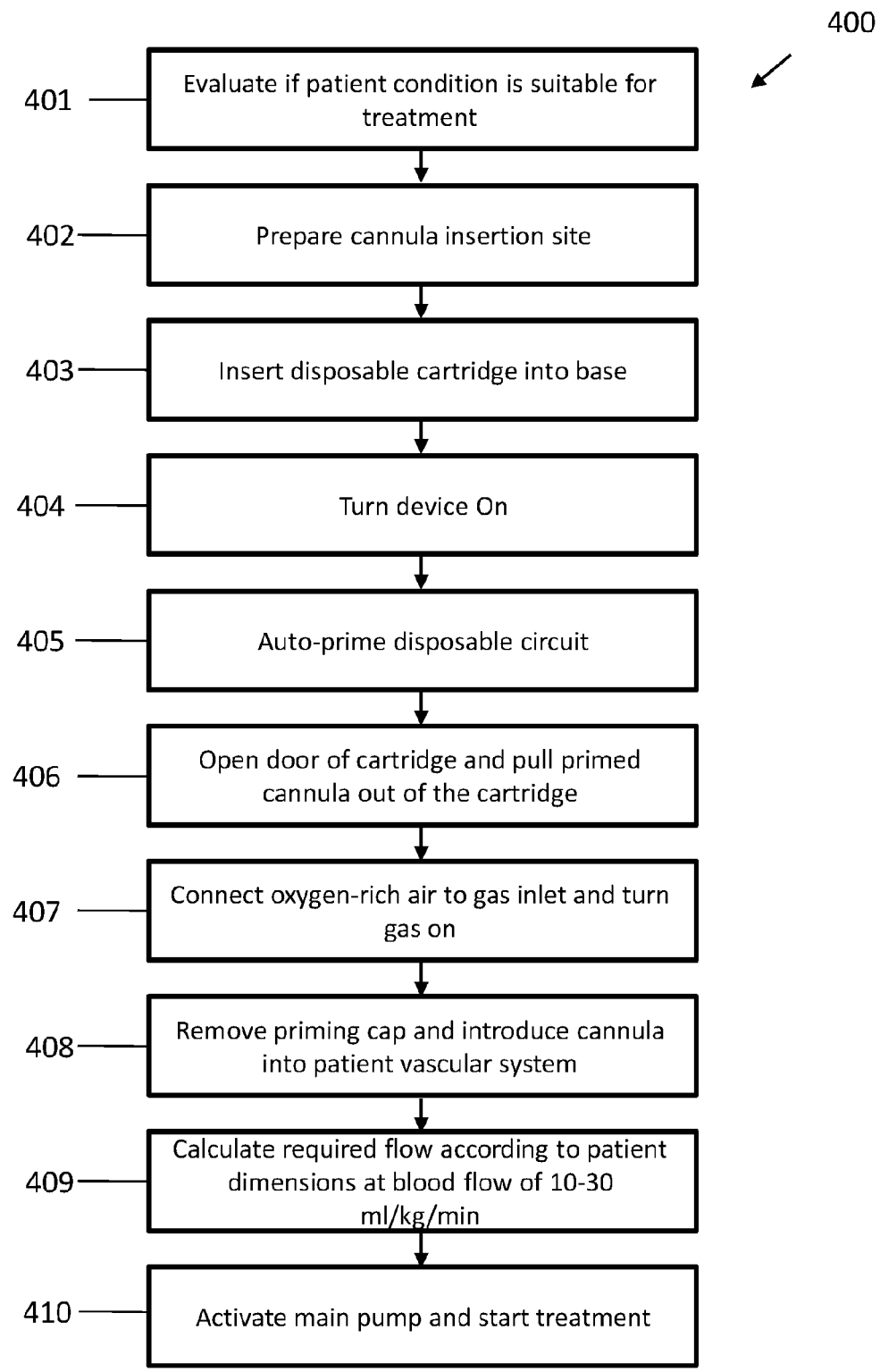
FIG. 4 depicts steps of a flow chart 400 for one optional method of operation of the extracorporeal system of FIG. 1.

FIG. 4 depicts steps of a flow chart 400 for one optional method of operation of the extracorporeal system of FIG. 1. At step 401 evaluation is made if the patient condition is appropriate for treatment with the extracorporeal oxygenation system of this invention according to parameters mentioned above. If the patient is identified as suitable for this treatment, at step 402 the medical team prepares the cannula insertion site for cannulation. At step 403 the disposable cartridge is being inserted into the base, and in step 404 the system is turned ON. At step 405 auto priming of the disposable circuit is conducted, and at step 406 the opening into the inner space of the cartridge is uncovered and the primed cannula is pulled out from the cartridge. At step 407 the Oxygen-rich gas supply is connected to the gas inlet within the cartridge and the gas flow is turned ON. At step 408 the cannula is inserted into the patient's vascular system, and at step 409 the required flow is calculated according to the patient's weight and dimensions at blood flow range of 10-30 ml/kg/min. at the next step 410 the main pumps are being activated and the treatment is started.

Figure 5A:
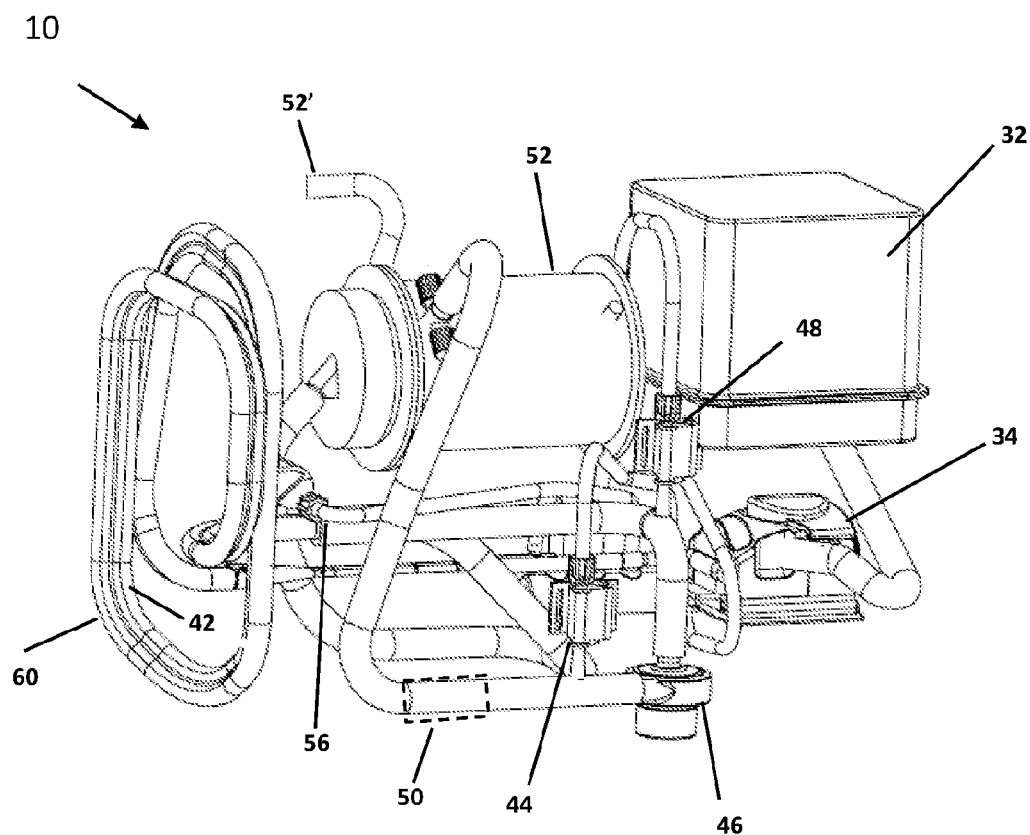
FIGS. 5A-5B are schematic isometric front view and isometric back view illustrations respectively of a cartridge having an auto priming system, according to embodiments of the present disclosure.
Figure 5B:
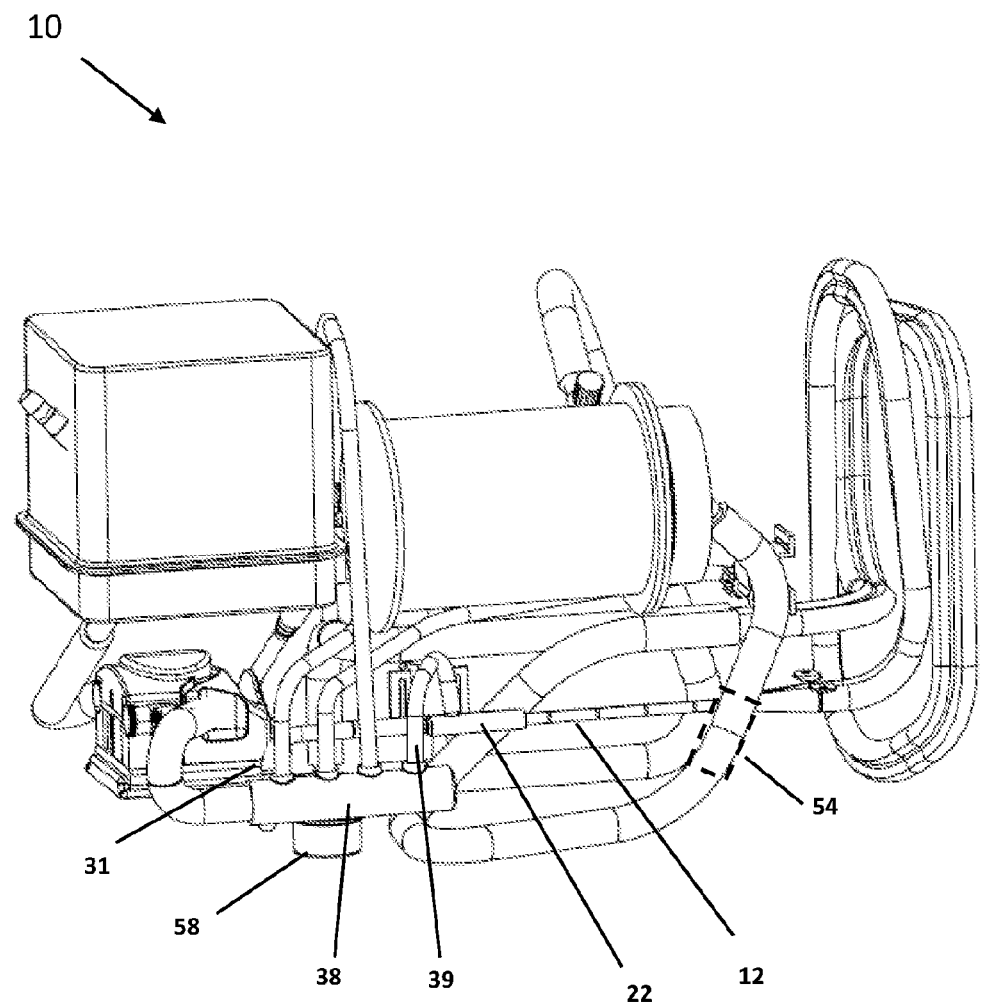

FIGS. 5A-5B are schematic isometric front view and isometric back view illustrations respectively of cartridge unit 10 having an auto priming system and a cannula, according to some optional embodiments of the present disclosure. In these drawings the housing is removed for clarity of description and the component comprised within the housing are shown. In this specific example, saline repository 32, which is connected via tubing 31 to priming cap 22. Saline repository 32 is connected to disposable pump head 34 of the priming pump, whose drive unit is part of base 10, as discussed above. From the priming pump head 34, the fluid path proceeds to two valves: pressure meter valve 36 (not shown in this view), and blood path valve 38. Pressure meter valve 36 is connected to three pressure meters 44, 48, 56. When pressure meter valve 36 is open, saline flows between pump head 34 and the pressure meters 44, 48, 56. When blood path valve 38 is open, fluid saline flows between pump head 34, via tubing 39, to priming cap 22, such that the fluid may continue to prime areas where blood will flow, following insertion of cannula 12 into a patient vascular system. After fluid enters priming cap 22, fluid enters the drainage lumen of cannula 12 and proceeds via tubing 42 to pressure meter 44. Following pressure meter 44, the fluid passes through blood pump head 46. The blood pump is used to adjust the pressure of fluid entering the oxygenator 52 so that the blood flows through the oxygenator at a desired rate. Before entering oxygenator 52, the fluid passes through a second pressure sensor 48. After exiting oxygenator 52, the fluid passes through a third pressure sensor 56. Prior to entering oxygenator 52, blood may optionally pass-through analyzer 50. Following oxygenation at the oxygenator 52, fluid passes through temperature sensor 54. Oxygenator 52 is connected to the gas supply by connector 52'.

Figure 6:
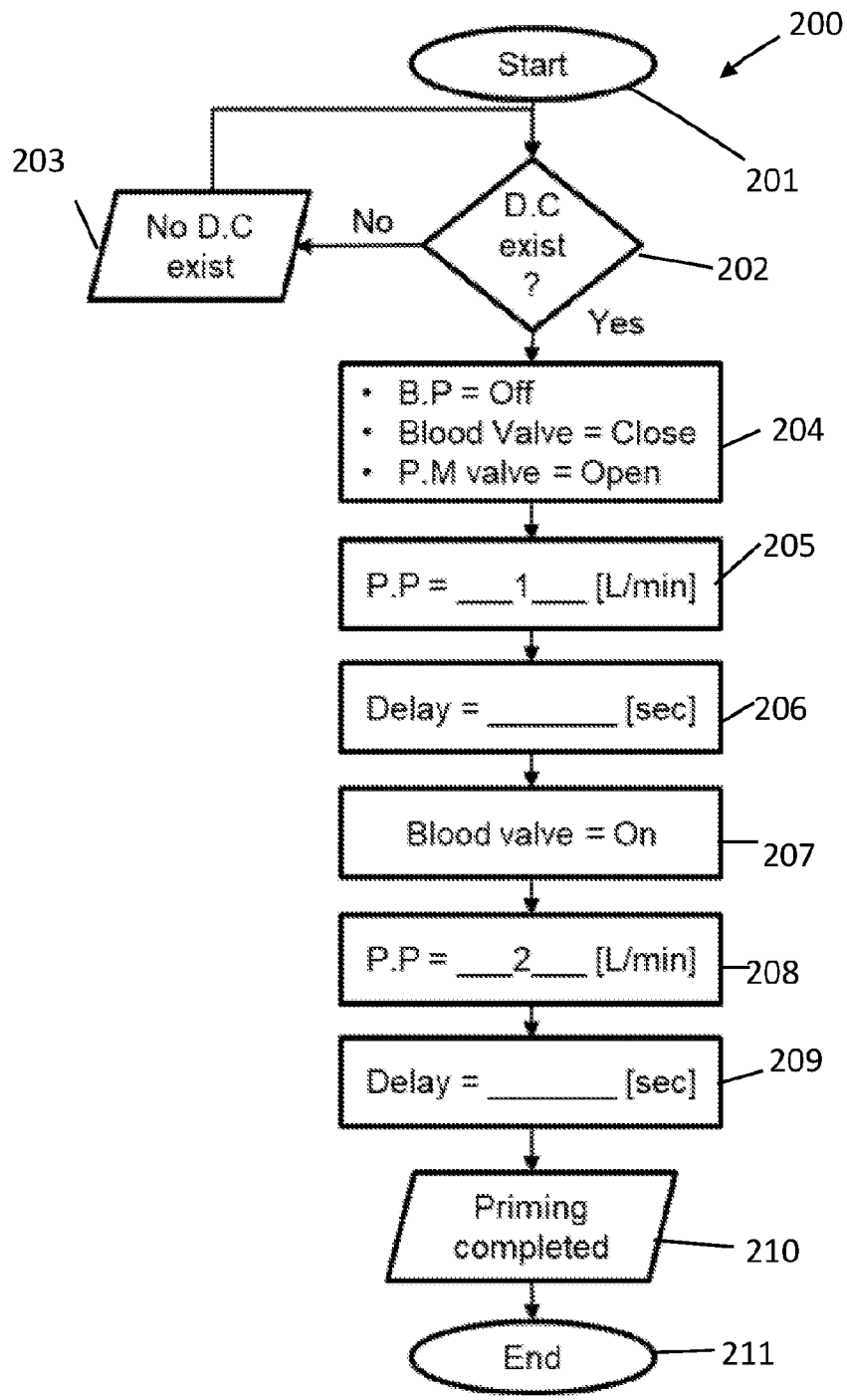
FIG. 6 depicts steps of a method of automatic priming of a cannula, according to embodiments of the present disclosure.

FIG. 6 illustrates exemplary steps of a flow chart 200 for automatic priming of the closed loop fluid flow system of cartridge 10. At step 201, the system is started. For example, a user may turn on controller 114. At step 202, controller 114 checks whether disposable cartridge 10 (abbreviated "D.C.") is operatively connected to the base 10. If no cartridge 10 is present, at step 203, the system returns to step 201, and remains ready for operation upon connection of a cartridge 10. If a cartridge 10 is identified, at step 204, the system turns the blood pump (abbreviated as "B.P.") off, closes the blood path valve 38, and opens the pressure meter valve 36 (abbreviated as "P.M. valve"). At step 205, optionally, the user sets the flow rate for the priming pump (abbreviated as "P.P."), for example 1 liter per minute. Alternatively, the system sets the flow rate automatically or uses a pre-set flow rate. The flow rate may be set, inter alia, based on criteria including the diameter of tubes between the pressure meter valve 36 and the pressure meters. At step 206, the user or system sets time parameters for operation of the priming pump (indicated as "delay") sufficient for fluid to fill all the lines between the pressure meter valve 36 and the pressure meters 44, 48, and 56, as shown in FIG. 2. The priming pump is then operated to fill these lines. At step 207, the system opens the blood path valve 38. At step 208, optionally, the user sets the flow rate for the priming pump, for example, as 2 liters per minute. This flow rate may be greater than the flow rate used in step 205, because the tubes in the blood path may have a greater diameter. Alternatively, as discussed above, the system sets the flow rate automatically or uses a pre-set flow rate. At step 209, user or system sets time parameters for operation of the priming pump (indicated as "delay") sufficient for air evacuated entirely from the closed loop. The priming pump is then operated, and fluid fills all the lines between the blood path valve 38, priming cap 22, the cannula 12, and the oxygenation system 40. The order of priming of the pressure meters 44, 48, 56, and the blood path may also be reversed so that the blood path is primed before the pressure meters. At steps 210 and 211, the priming is completed, and the process ends. In exemplary embodiments, the entire priming process takes up to approximately two minutes. Advantageously, the priming process may be performed entirely autonomously, without requiring any manual infusion of saline into the cannula or other system components. Alternatively, bubble sensor/s may be used to indicate that the priming process is completed.

Figure 7:
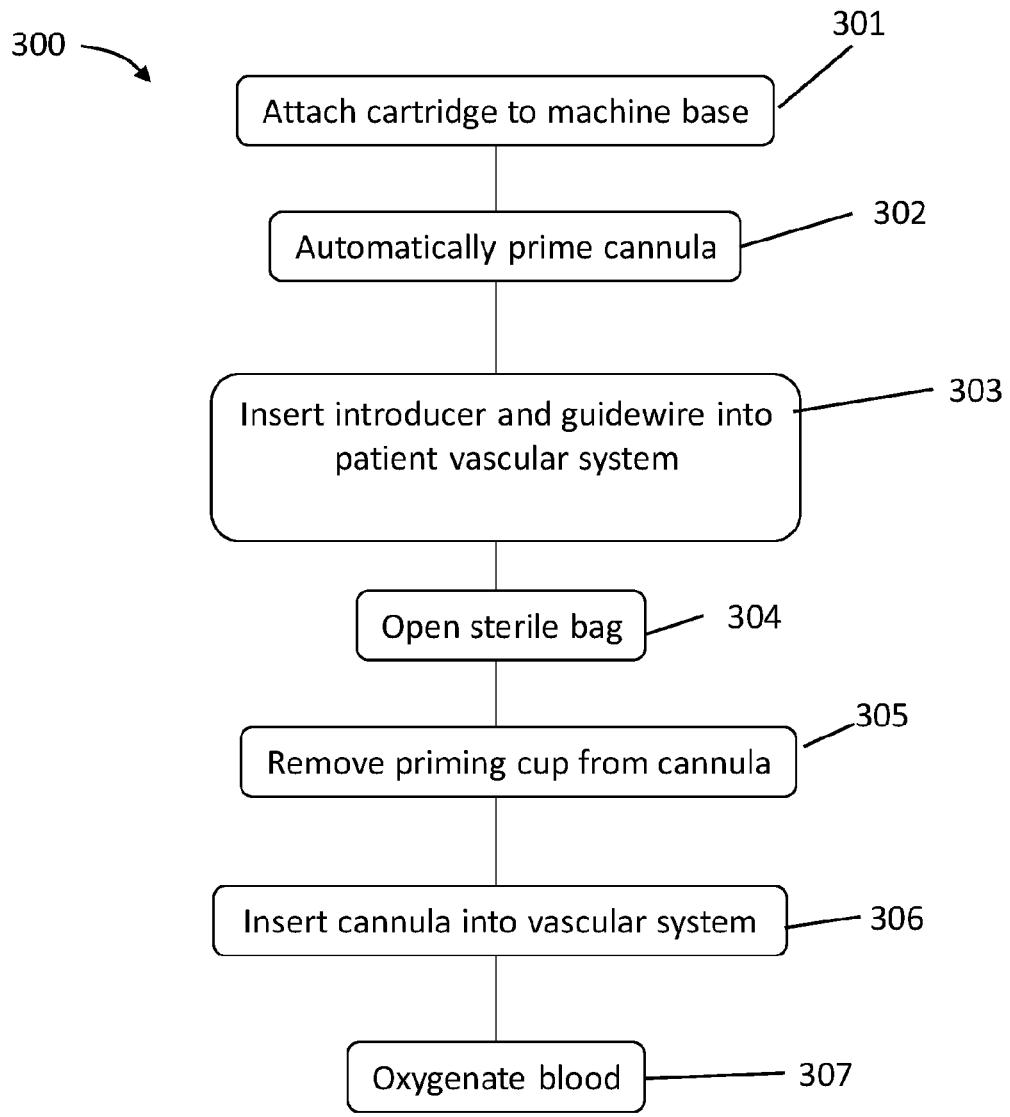
FIG. 7 depicts steps of a method of external oxygenation, according to embodiments of the present disclosure.

FIG. 7 illustrates exemplary steps of a method of automatic priming 300, as part of an overall process of external oxygenation of a patient, according to embodiments of the present disclosure.

At step 301, a user attaches cartridge 10 to base 110. At step 302, the machine primes the system, by operating the priming pump when the priming cap 22 is fitted over the cannula 12, in the manner described above. Advantageously, this priming operation may be commenced automatically, upon detection of attachment of the cartridge 10 to the base 110.

At step 303, a user (e.g., a surgeon or a nurse) opens patient penetration kit 130, and inserts introducer 132, dilators 134, and guidewire 136 into a patient vascular system. This insertion is performed in any typical manner known to those of skill in the art. For example, a surgeon may penetrate a 'patient's jugular vein or other blood vessel and expand the blood vessel using expanders with increasing diameters. The penetration is expanded until the diameter of the cannula 12 is reached.

At step 304, the user opens the cover of an opening in the cartridge to access cannula 12 and priming cap 22.

At step 305, the user removes priming cap 22 from the cannula 12. At this point, lumens 14, 16 are removed from the closed loop.

At step 306, the user inserts the cannula 12 into the 'patient's vascular system. For example, the surgeon may extract the expanders from the vascular system, leaving the guiding wire 136 in place. The sheath 18 is threaded over guidewire 136 until the cannula 12 is in the desired location within the 'patient's body. During the process of insertion of the cannula 12 into the patient vascular system, a small amount of saline may be drained from the ends 15, 17 of the lumens 14, 16, to ensure that no air is inserted into cannula 12. Following placement of the cannula 12, the surgeon stitches wings 20 of cannula 12 to the 'patient's skin, so that cannula 12 remains in place. The surgeon then removes guiding wire 136. Sheath 18 is then sealed (e.g., with a cap) or collapsed, so that no blood drains out of sheath 18. At step 307, the system 100 oxygenates blood.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above-described embodiments that would still be covered by the present invention.

The invention claimed is:

1. A system for automatic priming of at least one cannula, comprising at least:
   a. a priming cap including an inlet and an outlet that are sealed from each other when mounted on a cannula;
   b. a saline repository;
   c. a priming pump comprising a drive unit and a replaceable priming pump head; and
   d. a fluid path comprising sterile tubing between a first lumen and second lumen of the at least one cannula, said fluid path not including the priming cap; wherein the priming cap is removably fittable over the first and second lumens, such that, when the priming cap is fitted over the first and second lumens, the inlet is in fluid communication with the first lumen of the at least one cannula, and the outlet is in fluid communication with the second lumen of the at least one cannula, such that the at least one cannula, priming cap, saline repository, priming pump head, and fluid path form a closed loop for fluid flow, and when the priming cap is not fitted over the at least one cannula, the at least one cannula is insertable into a patient vascular system; and
   e. a controller configured to operate the priming pump when the priming cap is fitted over the at least one cannula, and thereby evacuate air from the closed loop.

2. The system according to claim 1, wherein the at least one cannula, the priming cap, the saline repository, the priming pump head, and the fluid path are contained within a cartridge, wherein said cartridge is attachable to and removable from a base containing the controller.

3. The system according to claim 2, wherein the controller is configured to commence a priming operation automatically upon attachment of the cartridge to the base.

4. The system according to claim 1, further comprising a sterile patient penetration kit, said sterile patient penetration kit including an introducer, one or more dilators, and a guidewire.

5. The system according to claim 4, wherein the controller is configured to operate the priming pump while the sterile patient penetration kit remains hermetically sealed.

6. The system according to claim 1, wherein the fluid path comprises an oxygenation system.

7. The system according to claim 6, wherein the first and second lumens comprise a drainage lumen and an infusion lumen, and, when the at least one cannula is inserted into a patient vascular system, the oxygenation system is configured to oxygenate blood withdrawn via the drainage lumen and return oxygenated blood via the infusion lumen.

8. The system according to claim 1, wherein the at least one cannula is a dual lumen cannula.

9. The system according to claim 1, wherein the closed loop comprises, in order, the first lumen, the fluid path, the second lumen, an inlet of the priming cap, the saline repository, the priming pump head, the outlet of the priming cap, and again the first lumen.

* * * * *